United States Patent [19]

Emerson et al.

[11] Patent Number: 5,399,493
[45] Date of Patent: Mar. 21, 1995

[54] METHODS AND COMPOSITIONS FOR THE OPTIMIZATION OF HUMAN HEMATOPOIETIC PROGENITOR CELL CULTURES

[75] Inventors: Stephen G. Emerson; Michael F. Clarke; Bernhard O. Palsson; Richard M. Schwartz, all of Ann Arbor, Mich.

[73] Assignee: The Regents of the University of Michigan, Ann Arbor, Mich.

[21] Appl. No.: 740,590

[22] Filed: Aug. 5, 1991

Related U.S. Application Data

[63] Continuation-in-part of Ser. No. 628,343, Dec. 17, 1990, abandoned, which is a continuation-in-part of Ser. No. 366,639, Jun. 15, 1989, abandoned, and a continuation-in-part of Ser. No. 737,024, Jul. 29, 1991, abandoned.

[51] Int. Cl.$^6$ .......................................... C12N 15/00
[52] U.S. Cl. ............................ 435/172.3; 435/240.2; 435/240.23
[58] Field of Search ............ 435/172.3, 240.2, 240.23, 435/240.3

[56] References Cited

U.S. PATENT DOCUMENTS

| | | |
|---|---|---|
| 4,481,946 | 11/1984 | Altshuler et al. . |
| 4,486,188 | 12/1984 | Altshuler et al. . |
| 4,963,489 | 10/1990 | Naughton et al. . |
| 5,032,407 | 7/1991 | Wagner et al. . |
| 5,032,508 | 7/1991 | Naughton et al. . |
| 5,199,942 | 4/1993 | Gillis . |

FOREIGN PATENT DOCUMENTS

| | | |
|---|---|---|
| 0358506 | 3/1990 | European Pat. Off. . |
| WO93/18136 | 9/1993 | European Pat. Off. . |
| WO93/18137 | 9/1993 | European Pat. Off. . |

OTHER PUBLICATIONS

Cell, vol. 47, pp. 3–10, Oct. 10, 1986, Yu–Chung Yang, et al., "Human IL-3 (Multi-CSF): Identification by Expression Cloning of a Novel Hematopoietic Growth Factor Related to Murine IL-3".

Migliaccio et al, Exp. Hematol (1990), vol. 18, pp. 1049–1055.

Isove et al, Exp. Cell. Res. (1980), vol. 126, pp. 121–125.

Dainiak et al, J. Clin. Invest. (1985), vol. 76, pp. 1237–1242.

Greenberger Joel, "Recent Modifications of Technique in ... Bone Marrow Cultures", Long–Term Bone Marrow Culture (1984), pp. 119–131.

Stead, Richard et al, "Canine Model for Gene Therapy (List continued on next page.)

Primary Examiner—Suzanne E. Ziska
Attorney, Agent, or Firm—Oblon, Spivak, McClelland, Maier, & Neustadt

[57] ABSTRACT

Methods, including culture media conditions, which provide for ex vivo human stem cell division and stable genetic transformation and/or the optimization of human hematopoietic progenitor cell cultures and/or increasing the metabolism or GM-CSF secretion or IL-6 secretion of human stromal cells are disclosed. The methods rely on culturing human stem cells and/or human hematopoietic progenitor cells and/or human stromal cells in a liquid culture medium which is replaced, preferably perfused, either continuously or periodically, at a rate of 1 ml of medium per ml of culture per about 24 to about 48 hour period, and removing metabolic products and replenishing depleted nutrients while maintaining the culture under physiologically acceptable conditions. Optionally growth factors are added to the culture medium.

20 Claims, No Drawings

OTHER PUBLICATIONS

... with Retroviral Vectors", Blood, vol. 71, No. 3, (Mar. 1988), pp. 742–747.

Boggs, Int. J. Cell Cloning (1990), vol. 8, pp. 80–96.

Kohn et al, Cancer Investigation (1989), vol. 7, pp. 179–192.

Lehn, Bone Marrow Transpl. (1990), vol. 5, pp. 287–293.

Verma, Sci. Amo. (Nov. 1990), pp. 68–84.

Gregory M. Springett, et al, "Infection Efficiency of T Lymphocytes with Amphotropic Retroviral Vectors is Cell Cycle Dependent," Journal of Virology, vol. 63, No. 9, pp. 3865–3869 (Sep. 1989).

James M. Wilson, et al, "Correction of CD18-Deficient Lymphocytes by Retrovirus-Mediated Gene Transfer," Science, vol. 248, pp. 1413–1416 (Jun. 15, 1990).

Helen R. Sunshine, et al, "Gelation of Sickle Cell Hemoglobin in Mixture with Normal Adult and Fetal Hemoglobins," J. Mol. Biol. 133, pp. 435–467 (1979).

Bruce A. Sullenger, et al, "Overexpression of Tar Sequences Renders Cells Resistant to Human Immunodeficiency Virus Replication," Coll, vol. 63, pp. 601–608 (Nov. 2, 1990).

Frank Grosveld, et al, "Position-Independent, High Level Expression of the Human b-Globin Gene in Transgenic Mice," Cell, vol. 51, pp. 975–985 (Dec. 24, 1987).

James M. Wilson, et al, "Expression of Human Adenosine Deaminase in Mice Reconstituted with Retrovirus-Transduced Hematopoietic Stem Cells," Proc. Natl. Acad. Sci. USA, vol. 87, pp. 439–443 (Jan. 1990).

"Expansion of Human Bone Marrow Progenitor Cells in a High Cell Density Continuous Perfusion System"; Bernhard O. Palsson, et al; Bio/Technology, vol. 11, Mar. 1993; pp. 368–372.

"Culture Perfusion Schedules Influence the Metabolic Activity and Granulocyte-Macrophage Colony-Stimulating Factor Production Rates of Human Bone Marrow Stromal Cells"; Jerry Caldwell, et al; Journal of Cellular Physiology; 147; pp. 344–353.

"Characterization and Partial Purification of Human Marrow Cells Capable of Initiating Long-Term Hematopoiesis In Vitro"; Heather J. Sutherland, et al; Blood; vol. 74, No. 5, Oct., 1989; pp. 1563–1570.

"Functional Characterization of Individual Human Hematopoietic Stem Cells Cultured at Limiting Dilution of Supportive Marrow Stromal Layers"; Heather J. Sutherland, et al; Proc. Natl. Acad. Sci. USA; vol. 87, May 1990; pp. 3584–3588.

"The Human Hematopoietic Stem Cell In Vitro and In Vivo"; C. J. Eaves, et al; Blood Cells; 18; 1992; pp. 301–307.

"Alternative Mechanisms With and Without Steel Factor Support Primitive Human Hematopoiesis"; H. J. Sutherland, et al; Blood; vol. 81, No. 6, Mar. 15, 1993; pp. 1464–1470.

"Human Recombinant Granulocyte-Macrophage Colony-Stimulating Factor: A Multilineage Hematopoietin"; Colin A. Sieff, et al; Science, vol. 230; Dec., 1985; pp. 1171–1173.

"Use of Limiting-Dilution Type Long-Term Marrow Cultures in Frequency Analysis of Marrow-Repopulating and Spleen Colony-Forming Hematopoietic Stem Cells in the Mouse"; Rob E. Ploemacher, et al; Blood, vol. 78, No. 10; Nov. 15, 1991; pp. 2527–2533.

"Evaluation of Hematopoiesis in Long-Term Bone Marrow Culture: Comparison of Species Differences"; C. E. Eastment, et al; Long-Term Bone Marrow Culture; 1984; pp. 97–118.

"Bone Marrow Stromal Fibroblasts Secrete Interleukin-6 and Granulocyte-Macrophage Colony-Stimulating Factor in the Absence of Inflammatory Stimulation: Demonstration by Serum-Free Bioassay, Enzyme-Linked Immunosorbent Assay, and Reverse Transcriptase Polymerase Chain Reaction"; Susan C. Guba, et al; Blood, vol. 80, No. 5; Sep. 1, 1992; pp. 1190–1198.

"Formation of haematopoietic microenvironment and haematopoietic stem cells from single human bone marrow stem cells"; Shiang Huang, et al; Nature, vol. 360; Dec. 24–31, 1992; pp. 745–749.

"Primitive hemopoietic stem cells: direct assay of most productive populations by competitive repopulation with simple binomial, correlation and covariance calculations"; David E. Harrison, et al; Experimental Hematology, 21; pp. 206–219.

"Methodology of Long-Term Culture of Human Hematopoietic Cells"; Connie J. Evans, et al; J. Tiss. Cult. Meth., 13; 1991; pp. 66–62.

"Expression of Human Adenosine Deaminase in Nonhuman Primates After Retrovirus-Mediated Gene Transfer"; Philip W. Kantoff, et al; J. Exp. Med., vol. 166; Jul., 1987; pp. 219–234.

"Mitogenic Effect of Bestatin on Lymphocytes"; Masaaki Ishizuka, et al; The Journal of Antibiotics, vol. XXXIII, No. 6; Jun., 1980; pp. 653–662.

(List continued on next page.)

OTHER PUBLICATIONS

"In Vitro Growth of Murine T Cells, II. Growth of in Vitro Sensitized Cells Cytotoxic for Alloantigens"; Steven A. Rosenberg, et al.; *The Journal of Immunology*, vol. 121, No. 5; Nov., 1978; pp. 1951–1955.

"Prospects for Human Gene Therapy"; W. French Anderson; *Science*, vol. 226; Oct., 1984; pp. 401–409.

"Granuloerythropoietic Colonies in Human Bone Marrow, Peripheral Blood, and Cord Blood"; A. A. Fauser, et al; *Blood*, vol. 52, No. 6; Dec., 1978; pp. 1243–1248.

"Induction of Colonies of Hemoglobin–Synthesizing Cells by Erythropoietin In Vitro"; John R. Stephenson, et al; *Proc. Nat. Acad. Sci. USA*, vol. 68, No. 7; Jul., 1971; pp. 1542–1546.

"The Basic Science of Gene Therapy"; Richard C. Mulligan; *Science*, vol. 260; May 14, 1993; pp. 926–932.

"A Cell Culture Model for T Lymphocyte Clonal Anergy"; Ronald H. Schwartz; *Science*, vol. 248; Jun. 15, 1990; pp. 1349–1356.

"Die Knochenmarkstammzellkultur Technische Voraussetzungen und klinische Einsatzmöglichkeiten"; Angelika Müller; *Folia Haematol*, Lepzig 116; 1989; pp. 731–743.

"Expansion of Primitive Human Hematopoietic Progenitors in a Perfusion Bioreactor System with IL-3, IL-6, and Stem Cell Factor"; Manfred R. Koller, et al; *Bio/Technology*, vol. 11; Mar., 1993; pp. 358–363.

"Beneficial Effects of Reduced Oxygen Tension and Perfusion in Long–Term Hematopoietic Cultures"; Manfed R Koller, et al; *Biochemical Engineering VII*, vol. 665 of the Annals of the New York Academy of Sciences; Oct. 13, 1992; pp. 105–116.

"Effects of Synergistic Cytokine Combinations, Low Oxygen, and Irradiated Stroma on the Expansion of Human Cord Blood Progenitors"; Manfred R. Koller, et al; *Blood*, vol. 80, No. 2; Jul. 15, 1992; pp. 403–411.

"Reduced Oxygen Tension Increases Hematopoiesis in Long–term Culture of Human Stem and Progenitor Cells from Cord Blood and Bone Marrow"; Manfred R. Koller, et al; *Experimental Hematology*, 20; 1992; pp. 264–270.

"Mammalian cell culture; engineering principles and scale–up"; M. W. Glacken, et al; *Trends in Biotechnology*, vol. 1, No. 4; 1983; pp. 102–108.

Anderson Science 226: 401.1984.

Adamson et al. Can Journal Chem Eng 64: 531, 1986.

Dexter Nature 309: 746, 1984.

Hoch et al Nature 320: 275, 1986.

Gartner et al PNAS 77(8): 4756, 1980.

METHODS AND COMPOSITIONS FOR THE OPTIMIZATION OF HUMAN HEMATOPOIETIC PROGENITOR CELL CULTURES

This application is a continuation-in-part of application Ser. No. 07/628,343, filed Dec. 17, 1990, now abandoned which is a continuation-in-part of application Ser. No. 07/366,639, filed Jun. 15, 1989, now abandoned which disclosures are incorporated herein by reference, and a continuation-in-part of application Ser. No. 07/737,024, filed Jul. 29, 1991, now abandoned.

BACKGROUND OF THE INVENTION

Field of the Invention

This invention relates to methods and compositions for the growth and transformation of mammalian cells in culture, particularly the growth and transformation of hematopoietic cell cultures.

Discussion of the Background

All of the circulating blood cells in the normal adult, including erythrocytes, leukocytes, platelets and lymphocytes, originate as precursor cells within the bone marrow. These cells, in turn, derive from very immature cells, called progenitors, which are assayed by their development into contiguous colonies of mature blood cells in 1–3 week cultures in semisolid media such as methylcellulose or agar. Progenitor cells themselves derive from a class of progenitor cells called stem cells. Stem cells have the capacity, upon division, for both self-renewal and differentiation into progenitors. Thus, dividing stem cells generate both additional primitive stem cells and somewhat more differentiated progenitor cells. In addition to the generation of blood cells, stem cells also may give rise to osteoblasts and osteoclasts, and perhaps cells of other tissues as well. This document described methods and compositions which permit, for the first time, the successful in vitro culture of human hematopoietic stem cells, which results in their proliferation and differentiation into progenitor cells and more mature blood cells.

In the late 1970s the liquid culture system was developed for growing hematopoietic bone marrow in vitro. The cultures are of great potential value both for the analysis of normal and leukemic hematopoiesis and for the experimental manipulation of bone marrow, for, e.g., retroviral-mediated gene transfer. These cultures have allowed a detailed analysis of murine hematopoiesis and have resulted in a detailed understanding of the murine system. In addition, it has made possible retroviral gene transfer into cultured mouse bone marrow cells. This allowed tagging murine hematopoietic cells proving the existence of the multi-potent stem cell and of the study of the various genes in the process of leukemogenesis.

But while it has been possible to transfer retroviral genes into cultured mouse bone marrow cells, this is not yet been possible in cultured human bone marrow cells because, to date, human long-term bone marrow cultures have been limited both in their longevity and in their ability to maintain stem cell survival and their ability to produce progenitor cells over time.

Human liquid bone marrow cultures were initially found to have a limited hematopoietic potential, producing decreasing numbers of progenitor cells and mature blood cells, with cell production ceasing by 6 to 8 weeks. Subsequent modifications of the original system resulted only in modest improvements. A solution to this problem is of incalculable value in that it would permit, e.g., expanding human stem cells and progenitor cells for bone marrow transplantation and for protection from chemotherapy, selecting and manipulating such cells, i.e., for gene transfer, and producing mature human blood cells for transfusion therapy.

Studies of hematopoiesis and in vitro liquid marrow cultures have identified fibroblasts and endothelial cells within adhering layers as central cellular stromal elements. These cells both provide sites of attachment for developing hematopoietic cells and can be induced to secrete hematopoietic growth factors which stimulate progenitor cell proliferation and differentiation. These hematopoietic growth factors include granulocyte colony stimulating factor (G-CSF), granulocyte-macrophage colony stimulating factor (GM-CSF) and interleukin-6 (IL-6).

Cultures of human bone marrow cells on such adherent layers in vitro however have been largely disappointing. Unlike related cultures from other species, such as mouse and tree shrew, human liquid marrow cultures fail to produce significant numbers of either nonadherent hematopoietic precursor cells or clonogenic progenitor cells for over 6 to 8 weeks. And although cultures lasting 3–5 months have been reported, no culture which stably produces progenitor cells from stem cells continuously for more than 4–6 weeks has been reported.

Moreover, nonadherent and progenitor cell production typically declined throughout even the short life of these cultures, so that it is not clear that stem cell survival or proliferation is supported at all by these cultures. Further, when studied in isolation, unstimulated bone marrow stromal cells secrete little if any detectable hematopoietfc growth factors (HGFs).

The lack of stable progenitor cell and mature blood cell production in these cultures has led to the belief that they are unable to support continual stem cell renewal and expansion. It has therefore been presumed that the cultures either lack a critical stem cell stimulant(s) and/or contain a novel stem cell inhibitor(s). But while explanations for failure to detect HGFs and uninduced stromal cell cultures have been suggested, the null hypothesis, which combines the failure to detect HGFs and the relative failure of human liquid marrow cultures, would be that the culture systems used in vitro do not provide the full range of hematopoietic supportive function of adherent bone marrow stromal cells in vivo.

Stem cell and progenitor cell expansion for bone marrow transplantation is a potential application for human long-term bone marrow cultures. Human autologous and allogenic bone marrow transplantation are currently used as therapies for diseases such as leukemia, lymphoma and other life-threatening disorders. For these procedures however, a large amount of donor bone marrow must be removed to insure that there is enough cells for engraftment.

A culture providing stem cell and progenitor cell expansion would reduce the need for large bone marrow donation and would make possible obtaining a small marrow donation and then expanding the number of stem cells and progenitor cells in vitro before infusion into the recipient. Also, it is known that a small number of stem cells and progenitor cells circulate in the blood stream. If these stem cells and progenitor cells could be collected by phoresis and expanded, then it would be possible to obtain the required number of stem cells and progenitor cells for transplantation from peripheral blood and eliminate the need for bone marrow donation.

Bone marrow transplantation requires that approximately $1 \times 10^8$ to $2 \times 10^8$ bone marrow mononuclear cells per kilogram of patient weight be infused for engraftment. This requires the bone marrow donation of the same number of cells which is on the order of 70 ml of marrow for a 70 kg donor. While 70 ml is a small fraction of the donors marrow, it requires an intensive donation and significant loss of blood in the donation process. If stem cells and progenitor cells could be expanded ten-fold, the donation procedure would be greatly reduced and possibly involve only collection of stem cells and progenitor cells from peripheral blood and expansion of these stem cells and progenitor cells.

Progenitor cell expansion would also be useful as a supplemental treatment to chemotherapy, and is another application for human long-term bone marrow cultures. The dilemma faced by oncologist is that most chemotherapy agents used to destroy cancer act by killing all cells going through cell division. Bone marrow is one of the most prolific tissues in the body and is therefore often the organ that is initially damaged by chemotherapy drugs. The result is that blood cell production is rapidly destroyed during chemotherapy treatment and chemotherapy must be terminated to allow the hematopoietic system to replenish the blood cell supply before a patient is retreated with chemotherapy. It may take a month or more for the once quiescent stem cells to raise up the white blood cell count to acceptable levels to resume chemotherapy during which case the drop in blood cell count is repeated. Unfortunately, while blood cells are regenerating between chemotherapy treatments, the cancer has time to grow and possibly become more resistant to the chemotherapy drugs due to natural selection.

To shorten the time between chemotherapy treatments, large numbers of progenitor and immature blood cells could be given back to the patient. This would have the effect of greatly reducing the time the patient would have low blood cell counts, thereby allowing more rapid resumption of the chemotherapy treatment. The longer chemotherapy is given and the shorter the duration between treatments, the greater the odds of successfully killing the cancer.

The hematopoietic cells required for progenitor cell expansion may come from either bone marrow withdrawal or peripheral blood collection. Bone marrow harvests would result in collection of approximately $4 \times 10^5$ CFU-GM progenitor cells. Phoresis of 5 liters of peripheral blood would collect approximately $10^5$ CFU-GM although this number could be increased to $10^6$ CFU-GM by prior treatment of the donor with GM-CSF. Rapid recovery of a patient would require transfusion of approximately $1 \times 10^8$ to $5 \times 10^8$ CFU-GM which is 100 to 1,000 times more than obtained by routine bone marrow donation or by peripheral blood donation. Therefore, expansion of bone marrow or peripheral blood to increase the number of CFU-GM 2 to 3 orders of magnitude would significantly affect chemotherapy administration and cancer treatment.

Gene therapy is a rapidly growing field in medicine which is also of inestimable clinical potential. Gene therapy has many potential uses in treating disease and has been reviewed extensively. See, e.g., Boggs, *Int. J. Cell Cloning.* (1990) 8:80–96, Kohn et al., *Cancer Invest.* (1989) 7 (2):179–192, Lehn, *Bone Marrow Transp.* (1990) 5:287–293, and Verma, *Scientific Amer.* (1990) pp. 68–84. Genetically transformed human stem cells have wide potential application in clinical medicine, as agents of gene therapy.

Gene therapy describes an emerging approach to clinical treatment which has evolved from earlier approaches in medical care. The earliest approaches to medical care, evolving over centuries, included gross surgical procedures and the administration of crude mixtures as medicinal agents. In the past century, biochemical pharmacology has supervened as the major method of medical treatment. Under this paradigm, pure biochemical molecules are delivered to the patient. In general, such pharmacologic agents act either as poisons (such as antimicrobials or cancer chemotherapy agents), physiologic mimetics which stimulate endogenous receptors (e.g., opiates, adrenergic agonists), or physiologic antagonists which block endogenous receptors (e.g. antihypertensives, anaesthetics).

Gene therapy is, by definition, the insertion of genes into cells for the purpose of medicinal therapy. The principle underlying gene therapy is to, rather than deliver doses of pharmacologic molecules, deliver a functional gene whose RNA or protein product will produce the desired biochemical effect in the target cell or tissue. There are several potential advantages of gene therapy over classical biochemical pharmacology. First, inserted genes can produce extremely complex molecules, including RNA and protein, which can be extraordinarily difficult or impossible to administer and deliver themselves. Next, controlled insertion of the desired gene into specific target cells can control the production of gene product to defined tissues. Finally, gene therapy can in principle be permanent within an individual, as the gene will continue to function in the target cells and their progeny.

There are several problems that must therefore be addressed for successful gene therapy. The first is to be able to insert the desired therapeutic gene into the chosen cells. Second, the gene must be adequately expressed in the target cell, resulting in the appropriate levels of gene product. Finally the RNA or protein produced must be properly processed by the target cell so that it is functional, i.e. so that gene therapy actually infers clinical therapy. Several methods of gene insertion into human cells in vitro are listed in Table 1.

TABLE 1

| | Comparison of DNA transfer methods. | | |
|---|---|---|---|
| Variable | Microinjection | Electroporation | Retrovirus |
| Efficiency | 10–100% | 0.0001–1% | 1–100% (depends on titer) |
| Effort | High | Low | Intermediate |

TABLE 1-continued

Comparison of DNA transfer methods.

| Variable | Microinjection | Electroporation | Retrovirus |
| --- | --- | --- | --- |
| Expense | High | Low | Intermediate |
| Stability | Good | Good | May be inactivated or become infective |
| DNA synthesis | ? | ? | Required |
| Size of DNA input | Not restricted | Not restricted | Limited ($\leq 8$ kb) |
| Need extraneous DNA | No | No | Yes |

Other techniques, such as homologous recombination, are being developed as well in many laboratories. Research in gene therapy has been on-going for several years in several types of cells in vitro, progressed to animal studies, and has recently entered the first human clinical trial(s).

The hematopoietic system is an ideal choice as a delivery system for gene therapy. Hematopoietic cells are readily accessible, simply by bone marrow aspiration or by peripheral blood mononuclear cell harvest. Once the genetic insertion is accomplished in vitro the treated cells can be reinfused intravenously, after which the genetically transformed cells will home to and develop in the bone marrow. Since mature blood cells circulate throughout the body, the genetically modified cells can deliver the specific gene product to any desired tissue.

Most importantly, hematopoietic tissues contain stem cells, which possess extensive (perhaps unlimited) capacities for self-renewal. This implies that if genetic material were stably transduced into these stem cells, then upon reinfusion of the hematopoietic tissue, these altered stem cells can expand and repopulate the marrow with cells that express the new gene. This leads to long-lasting, perhaps lifelong delivery of the desired gene product. Similarly, successful stable gene transfer into stem cells located in other tissues, or into embryonic stem cells, likewise leads to long-lasting gene product delivery.

Successful hematopoietic stem cell gene therapy has broad application, to both diseases specific to the hematopoietic system and to other organ system diseases. Within the hematopoietic system, both inherited and acquired diseases can be treated by stem cell gene therapy. For example, hemoglobin deficiencies such as α and β Thalessemias could be treated by the insertion of the gene coding for the globin α or β chain, together with regulatory sequences that confer high level tissue specific erythrocytes (see, Grosveld et al, Cell (1987) 51:975-986). Similarly, sickle cell anemia could be corrected by the genetic insertion of the fetal globin gene into hematopoietic stem cells, as the regulated expression of high levels of fetal hemoglobin are sufficient to prevent sickling in red cells despite the copresence of sickle hemoglobin (see, Sunshine et al, J. Molec. Biol. (1979) 133:435).

Genetic disease of neutrophils caused by functional protein deficiencies, such as leukocyte adhesion deficiency (LAD) or chronic granulomatous disease (CGD) could be treated by the genetic insertion of the gene encoding the defective or absent gene, along with regulatory DNA sequences that confer high level, tissue specific expression into hematopoietic stem cells (see, Wilson et al, Science (1990) 248:1413-1416). Genetic diseases involving platelets, such as von Willebrands' Disease, could be corrected by the genetic insertion of the gene encoding, e.g. von Willebrands' Factor, along with sequences which permit its expression and secretion.

The particular suitability of hematopoietic stem cell gene therapy for the replacement of congenitally deficient gene products is particularly evident in the treatment of lymphocyte immunodeficiency diseases, such as severe combined immunodeficiency due to adenosine deaminase deficiency. Retroviral gene therapy of circulating T cells with the ADA gene has been found to be successful at reducing the clinical immunodeficiency experienced by these patients, but the effects are only temporary because the transfected T lymphocytes have a finite life span in vivo (see, Kasid et al, Proc. Nat. Acad. Sci. (USA) (1990) 87:473-477, or Culver et al Proc. Nat. Acad. Sci. (USA), (1991) 88:3155-3159). If, however, the gene could be successfully transfected into hematopoietic stem cells, then all of the T cells which arose from these stem cells would contain and express the ADA gene. Therefore, since the transfected stem cells would persist and proliferate for the life of the patient, the T cell ADA deficiency would be permanently treated by a single gene transfer stem cell treatment (see, Wilson et al, Proc. Natl. Acad. Sci., (U.S.A.) (1990) 87:439-443).

In addition to treating inherited enzymatic abnormalities of the hematopoietic system, stem cell gene therapy could be useful for protecting stem cells and their progeny from toxic exogenous agents such as viruses or chemotherapy. For example, gene transfer of DNA sequences encoding the TAR binding site of the HIV TAT transactivating factor have been shown to protect T cells from spreading infection by the HIV virus (see, Sullenqer et al, Cell (1990) 63:601-608). Stable transaction of these sequences into hematopoietic stem cells would result in a pool of T cells, all arising from these stem cells, which were relatively or absolutely resistant to the spread of HIV.

Similarly, successful transfection of the genes encoding the multi-drug resistance gene (MDR) or the methotrexate resistance gene into human bone marrow stem cells would create stem cells which were relatively resistant to the effects of cancer chemotherapy. Following autologous bone marrow transplantation with these genetically manipulated cells, patients would be able to tolerate chemotherapy with the agents to which their stem cells were protected with suffering the profound bone marrow suppression commonly caused by these anti-cancer drugs. This would enable patients to receive more effect doses of cancer chemotherapy with less toxicity.

One can readily envision that hematopoietic stem cell gene therapy will also be useful for acquired hematopoietic disease such as leukemia, lymphoma and aplastic anemia. Once the genetic causes of these diseases is discovered, insertion of a gene whose product either overcomes that of the abnormal gene in the cell or corrects it directly (perhaps by splicing out and replacing the gene) would correct the abnormality.

On a broader level, however, hematopoietic stem cell gene therapy can be useful for the treatment of diseases outside the hematopoietic system as well. Gene transfer of DNA sequences carrying therapeutic soluble proteins could give rise to mature blood cells which permanently secreted the desired amounts of a therapeutic molecule. By way of examples, this approach could be useful for the treatment of, e.g., diabetes mellitus by the insertion of DNA sequences for insulin along with regulatory DNA sequences that controlled the proper expression of the transfected insulin gene, perhaps in response to elevated plasma glucose levels. Systemic hypertension could be treated by genetic insertion of stem cells with DNA sequences encoding secretory peptides which act as competitive inhibitors to angiotensin converting enzyme, to vascular smooth muscle calcium channels, or to adrenergic receptors. Alzheimer's disease could possibly be treated by genetic insertion into stem cells of DNA sequences encoding enzymes which break down amyloid plaques within the central nervous system.

The many applications of gene therapy, particularly via stem cell genetic insertion, are thus well known and have been extensively reviewed (see, Boggs et al, supra, Kohn et al, supra, Lehn, supra, and/or Verma et al, supra). There are indeed increasing examples of some success in achieving therapeutic gene transfer into differentiated human stem cells, as described for example in T lymphocytes (see, Kalsd et al, Proc. Nat. Acad. Sci. (U.S.A.), (1990) 87:473–477, Culver et al, Proc. Nat. Acad. Sci. (U.S.A.) (1991) 88:3155–3159).

Unfortunately, achieving (stable) gene transfer into human stem cells has not been accomplished prior to the present invention. While several groups have demonstrated the feasibility of retroviral mediated gene transfer into human hematopoietic cells, human primitive hematopoietic stem cells have not been successfully transfected. This is in sharp contrast to experiments in the mouse, in which some level of retrovirally mediated gene transfer into hematopoietic stem cells has been possible (see, Wilson et al, Pro. Nat. Acad. Sci. (USA) (1990) 87:439–443).

The major impediment to achieving successful human hematopoietic stem cell gene therapy has been the inability to insert genes into human hematopoietic cells under conditions in which the stem cells are dividing and proliferating. Successful stable gene insertion into a target cell requires that the target cell undergo at least one round of cell division. Thus if stem cells are not dividing in the presence of the desired genetic material, the material will not be stably inserted into the stem cells. Prior to the development of the present invention, no system existed which supported the ex vivo division and proliferation of human stem and no successful genetic transformation of human stem cells has been possible.

There is therefore a considerable need for methods and compositions for the ex vivo replication and stable genetic transformation of human stem cells and for the optimization of human hematopoietic progenitor cell cultures, particularly in light of the great potential for stem cell expansion, progenitor cell expansion, and gene therapy offered by these systems. Unfortunately, to date, attempts to achieve such results have been disappointing.

SUMMARY OF THE INVENTION

Accordingly, it is an object of this invention to provide novel methods, including culture media conditions, for the ex vivo replication and stable genetic transformation of human stem cells.

It is another object of this invention to provide novel methods, including culture media conditions, for the optimization (i) of human hematopoietic progenitor cell cultures and (ii) of obtaining stably genetically transformed human hematopoietic progenitor cells.

The present invention is based on the inventors' discovery of novel methods, including culture media conditions, which provide for ex vivo human stem cell division and stable genetic transformation and/or the optimization of human hematopoietic progenitor cell cultures. These methods rely on culturing human stem cells and/or human hematopoietic progenitor cells in a liquid culture medium which is replaced, preferably perfused, either continuously or periodically, at a rate of 1 milliliter (ml) of medium per ml of culture per about 24 to about 48 hour period, and removing metabolic products and replenishing depleted nutrients while maintaining the culture under physiologically acceptable conditions. In a particularly preferred embodiment of the present invention, the above medium replacement rate is used in conjunction with the addition of hematopoietic growth factors to the rapidly exchanged culture medium.

The inventors have discovered that the increased medium exchange rate used in accordance with the present invention, with the optional addition of hematopoietic growth factors to the rapidly exchanged culture medium, surprisingly (1) supports cultures in which human stem cells proliferate over extended periods of time of at least 5 months, (2) supports cultures in which human hematopoietic progenitor cells are produced by division and differentiation of human stem cells through extended culture periods of at least 5 months, and (3) stimulates the increased metabolism of and GM-CSF secretion from human stromal cells, including human bone marrow stromal cells. The present invention provides, for the first time, human stem cell survival and proliferation in culture.

The present invention also provides an ex vivo culture system which supports the continuous proliferation of human stem cells to allow the successful insertion of genetic material into the human stem cells, resulting in the creation of stably genetically transformed human stem cells. This embodiment of the invention can be used for the transfer of any genetic material that can be engineered into a recombinant retrovirus, or any other gene transfer vector that requires cell division. Genetically modified human stem cells produced in this manner can be applied to a wide variety of clinical diseases, as described supra.

The invention also provides methods for enhancing the efficiency of genetic transfer into human hematopoietic progenitor cells, together with providing stably genetically transformed human stem cells and/or stably genetically transformed human hematopoietic progenitor cells.

DESCRIPTION OF THE PREFERRED EMBODIMENTS

The advantages of the present invention may be observed whenever the present invention is applied to any standard system for liquid human stem and/or progenitor cell culture, such as those found in hematopoietic culture(s). By the use of the rapid medium exchange rates used in accordance with the present invention, with the optional addition of supplementary hematopoietic growth factors to the culture, the inventors have surprisingly discovered that one is able to make standard systems for liquid human hematopoietic cultures, which comprise cultures performed in the presence or absence of animal sera or plasmas, including horse, calf, fetal calf, or human serum, perform in a qualitatively superior manner.

Human liquid hematopoietic cultures which may be used in accordance with the invention can be performed at cell densities of from $10^4$ to $10^9$ cells per ml of culture, using standard known medium components such as, for example, IMDM, MEM, DMEM, RPMI 1640, Alpha Medium or McCoy's Medium, which can use combinations of serum albumin, cholesterol and/or lecithin, selenium and inorganic salts. As known, these cultures may be supplemented with corticosteroids, such as hydrocortisone at a concentration of $10^{-4}$ to $10^{-7}$ M, or other corticosteroids at equal potent dose, such as cortisone, dexamethasome or solumedrol. These cultures are typically carried out at a pH which is roughly physiologic, i.e. 6.9 to 7.4. The medium is typically exposed to an oxygen-containing atmosphere which contains from 4 to 20 vol. percent oxygen, preferably 6 to 8 vol. percent oxygen.

Using these standard culture techniques, the cell mass used may be enriched, by any desired amount, such as by up to $10^3$ fold or more, either for stem cell content or for hematopoietic progenitor cell content. Different known methods may be used to achieve this enrichment, corresponding either to a negative selection method or a positive selection method. For example, in accordance with the negative selection method, mature cells are removed using immunological techniques, e.g., labelling non-progenitor, non-stem cells with a panel of mouse anti-human monoclonal antibodies, then removing the mouse antibody-coated cells by adherence to rabbit-anti-mouse Ig-coated plastic dishes. See e.g., Emerson et al, *J. Clin. Invest.* (1985) 76:1286–1290.

The present invention relies on a fundamental alteration of the conditions of liquid human bone marrow cultures under any of the above conditions; rapid replacement of the nutrient medium. Standard culture schedules call for medium and serum to be exchanged weekly, either as a single exchange performed weekly or a one-half medium and serum exchange performed twice weekly. In accordance with the present invention, the nutrient medium of the culture is replaced, preferably perfused, either continuously or periodically, at a rate of about 1 ml per ml of culture per about 24 to about 48 hour period, for cells cultured at a density of from $2 \times 10^6$ to $1 \times 10^7$ cells per ml. For cell densities of from $1 \times 10^4$ to $2 \times 10^6$ cells per ml the same medium exchange rate may be used. For cell densities higher than $10^7$ cells per ml, the medium exchange rate may be increased proportionally to achieve a constant medium and serum flux per cell per unit time.

Replacement of the nutrient medium in accordance with the invention may be carried out in any manner which will achieve the result of replacing the medium, e.g., by removing an aliquot of spent culture medium and replacing it with a fresh aliquot. The flow of the aliquot being added may be by gravity, by pump, or by any other suitable means. The flow may be in any direction or multiplicity of directions, depending upon the configuration and packing of the culture. Preferably, the new medium is added to the culture in a manner such that it contacts the cell mass. Most preferably, it is added the culture in a manner mimicking in vivo perfusion, i.e., it is perfused through at least part of the cell mass and up to the whole cell mass.

Another, optional but important, embodiment of the present invention, resides in the addition of hematopoietic growth factors, including synthetic hematopoietic growth factors, to the rapidly exchanged cultures. In a particularly preferred aspect of this embodiment, the cytokines IL-3 and GM-CSF are both added, together, to the medium at a rate of from 0.1 to 100 ng/ml/day, preferably about 0.5 to 10 ng/ml/day, most preferably 1 to 2 ng/ml/day. Epo may be added to the nutrient medium in an amount of from 0.001 to 10 U/ml/day, preferably 0.05 to 0.15 U/ml/day. Mast cell growth factor (MCGF, c-kit ligand, Steel factor), may be added to the medium in an amount of from 1 to 100 ng/ml/day, preferably 10 to 50 ng/ml/day. IL-1 ($\alpha$ or $\beta$) may also be added in an amount of from 10 to 100 units/ml per 3 to 5 day period. Additionally, IL-6, G-CSF, basic fibroblast growth factor, IL-7, IL-8, IL-9, IL-10, IL-11, PDGF, or EGF to be added, at a rate of from 1 to 100 ng/ml/day.

The inventors have discovered that when IL-3, GM-CSF and Epo are used as described above one obtains lineage specific development of red blood cells. Alternatively, when IL-3 and GM-CSF, with or without IL-6 or G-CSF, are used, the culture preferentially produce granulocytes. The inventors also observed that with the cultures of the invention T and B lymphocytes are lost over time.

The metabolic product level in the medium is normally maintained within a particular range. Glucose concentration is usually maintained in the range of about 5 to 20 mM. Lactate concentration is usually maintained below 35 mM. Glutamine concentration is generally maintained in the range of from about 1 to 3 mM. Ammonium concentration is usually maintained below about 2.4 mM. These concentrations can be monitored by either periodic or on-line continuous measurements using known methods. See, e.g., Caldwell et al, *J. Cell. Physiol.* (1991) 147:344–353.

The cells which may be cultured in accordance with the present invention may be any human stem cells or human stem cell-containing cellular mass, including human peripheral blood mononuclear cells, human bone marrow cells, human fetal liver cells, embryonic stem cells and/or human cord blood cells. Each of these cell masses contains human stem cells and/or human hematopoietic progenitor cells. Other cellular masses containing human stem cells may also be used in accordance with the invention, including any human stem cell found in human bone marrow.

In a preferred embodiment of the invention, the cell culture may be enriched to augment the human stem cell content of the cell mass. Such enrichment may achieved as described above, and, when used in accordance with the invention, provides the first useful means for genetic therapy via gene transfer into human stem cells, including human stem cells present in human bone marrow and human bone marrow stem cells. Stem cells present in human bone marrow are cells obtainable from human bone marrow, peripheral blood, fetal liver, or human cord blood.

Generally, in this embodiment, a packaging cell line infected with a retrovirus, or a supernatant obtained from such a packaging cell line culture, or an other gene transfer vector, is added to human stem cells cultured in accordance with of the invention to obtain stably genetically transformed human stem cells. The present invention provides increased levels of stem cell and human hematopoietic progenitor cell replication, whereas, by contrast, prior cultures provided only for human hematopoietic progenitor cell replication at a decreasing rate (i.e., decaying cultures). The present culture system provides, for the first time, expansion of cells in culture, which is required for retroviral infection of cells. Earlier systems in which retroviral infection was carried out on decaying cultures provided no infection of earlier cells. The present invention, particularly when it is practiced together with an enriched stem cell pool, and even more particularly when it is practiced still further with the use of hematopoietic growth factors, including synthetic growth factors, provides a very effective means for obtaining stem cell infection in vitro.

The inventors have discovered that addition of supernatants containing recombinant retroviruses to the cultures results in the introduction of the viruses and the genes they carry into human (hematopoietic) stem cells. The progenitor cells which arise by division and differentiation from these stem cells, and the mature blood cells which arise from further division and differentiation of these progenitor cells, contain the transfected DNA throughout the period of the hematopoietic culture in vitro. The inventors have observed that when the retrovirus is only added at the beginning period of the culture, they obtain transfected progenitors and mature blood cells which can arise only from stem cells present, proliferating and stably, genetically transformed in the beginning of the culture, because no retrovirally infected cell can infect an adjacent cell. Progenitor cells and more mature cells containing the desired genetic material have accordingly received the gene from the more primitive stem cells genetically transformed during the initial retroviral infection period.

In a preferred embodiment of this aspect of the invention, human hematopoietic cells, either isolated from bone marrow, peripheral blood, fetal liver, or umbilical cord blood, are first enriched for the presence of stem cells by removing more mature blood cells. This is accomplished by incubating the hematopoietic cells with muring monoclonal antibodies recognizing epitopes on mature blood cells and bone marrow precursor cells but not stem cells, and then removing the labelled cells by immunoadherence to a rabbit-anti-mouse-Ig immunoadsorbent surface. The resultant lineage negative (Lin−) cells are then cultured in the presence of a retrovirus or other gene transfer vector in accordance with the invention. Preferably the culture is carried out in the presence of GM-CSF (preferably 1 mg/ml/day) and IL-3 (preferably 1 mg/ml/day) with or without IL-1 (preferably 50 U/ml/4 day period), with or without c-kit ligand (Mast cell growth factor) (preferably 10 ug/ml/day).

The retroviral infection may be performed by either including into the culture medium, supernatants (e.g., 5 to 20% vol/vol) produced by retroviral packaging cell lines infected with recombinant retrovirus, during the first 2 to 21, preferably 10 to 14 days of the culture, or by culturing the Lin− cells directly over the infected retroviral packaging lines themselves, or by both.

Preferably, retroviral supernatants are used, and the period of incubation in the presence of virus is 12 to 16 days. Also preferably, the packaging cell lines are grown to near confluency, the medium exchanged, and the cell lines further incubated for 12 to 15 hours. The medium is then collected and used in the transfection of the human stem cells. However, this protocol is not strictly required and any supernatant produced by a retroviral packaging cell line may be used. Any (known) retroviral packaging cell lines may be used in accordance with the invention and cultured in accordance with any known protocol (see, e.g., Wilson et al, *Science* (1990) 248:1413–1416 and/or Sullenger et al, *Cell* (1990) 63:601–608). Illustrative packaging cell lines include NIH 3T3 cells and renal carcinoma cell line 5637.

Any gene which is inserted into a recombinant retrovirus together with suitable promoter and enhancer elements that permit its expression can be incorporated into human stem and hematopoietic progenitor cells. The invention provides for the first time conditions that permit stem cell survival and proliferation in these cultures, permitting the creation of stably transfected, genetically modified human hematopoietic stem cells in these cultures. The terms "stably transformed" and "stably transfected" are used in this text to designate incorporation of exogenous DNA into the human stem cell chromosome(s), made possible by the present invention because it permits exposing dividing human stem cells ex vivo to such exogenous DNA.

In accordance with the present invention one obtains cultures in which human hematopoietic progenitor cells are produced by division and differentiation from human stem cells throughout a culture period of at least five months. That is, one obtains a culture which supports stem cell survival and proliferation in culture.

Data obtained by the inventors indicates that medium perfusion rate is a very significant variable in determining the behavior of ex vivo human bone marrow cultures. This data showed that when the medium exchange rate was increased from the traditional once per week Dexter rate to a daily medium exchange rate of 7 volumes per week, a significant effect on ex vivo hematopoiesis is obtained. In experiments carried out by the inventors, all cultures displayed a significant loss of cells during the first 3 to 4 weeks. Following this decay, the cultures stabilized and the effect of a medium perfusion rate became more pronounced.

A 3.5 per week medium exchange rate led to the most prolific cultures and also to cultures of greatest longevity in terms of progenitor cell production. Of particular note, during weeks 4 to 10, the biweekly number of nonadherent cells produced was actually stable or increasing.

Over the entire course of the cultures, the cumulative number of cells produced after week 3.5 was almost three-fold greater than that which is produced under the traditional Dexter culture protocol. Further, stable production of progenitor cells is maintained until week 18.

Human stromal cells, such as stromal cells found in human bone marrow, may or may not be present in the cultures of the invention. In typical cultures, stromal cells are present in the cell culture in an amount of approximately $10^{-3}$ to $10^{-1}$ (stromal cells/total cells).

In another aspect of the invention, the inventors discovered that the cultures of the invention surprisingly provide increased metabolism and GM-CSF and IL-6 secretion from human bone marrow stromal cells. Whereas no GM-CSF is detected in human bone marrow stromal cells supernatant, rapid medium exchange in accordance with the invention stimulates human bone marrow stromal cells to secrete 300 centograms/ml/day to 200 picograms/ml/day of GM-CSF. Secretion of IL-6 by human bone marrow stromal cells is also increased by rapid medium exchange in accordance with the invention from 1 to 2 ng/ml/day to 2 to 4 ng/ml/day. This increase is observed both when only the rapid medium exchange rate of the invention is used, and when the rapid exchange rate together with the addition of hematopoietic growth factors is used. On the basis of data obtained by the inventors, the effect of the rapid medium exchange rates of the invention on human stromal cell production of cytokines should be observed with human stromal cells in any complex tissue culture system.

Illustratively, the medium used in accordance with the invention may comprise three basic components. The first component is a media component comprised of IMDM, MEM, DMEM, RPMI 1640, Alpha Medium or McCoy's Medium, or an equivalent known culture medium component. The second is a serum component which comprises at least horse serum or human serum and may optionally further comprise fetal calf serum, newborn calf serum, and/or calf serum. The third component is a corticosteroid, such as hydrocortisone, cortisone, dexamethasome, solumedrol, or a combination of these, preferably hydrocortisone.

The compositional make up of various media which can be used are set forth below.

| Iscove's Modified Dulbecco's Media (IMDM)[1,2,3] | | |
|---|---|---|
| COMPONENT | 380-2440 1X Liquid mg/L | 430-2200 Powder mg/L |
| INORGANIC SALTS: | | |
| $CaCl_2$ (anhyd.) | 165.00 | 165.00 |
| KCl | 330.00 | 330.00 |
| $KNO_3$ | 0.076 | 0.076 |
| $MgSO_4$ (anhyd.) | 97.67 | 97.67 |
| NaCl | 4505.00 | 4505.00 |
| $NaHCO_3$ | 3024.00 | — |
| $NaH_2PO_4 \cdot H_2O$[a] | 125.00 | 125.00 |
| $Na_2SeO_3 5H_2O$ | 0.0173 | 0.0173 |
| OTHER COMPONENTS: | | |
| D-Glucose | 4500.00 | 4500.00 |
| Phenol red | 15.00 | 15.00 |
| HEPES | 5958.00 | 5958.00 |
| Sodium pyruvate | 110.00 | 110.00 |
| AMINO ACIDS: | | |
| L-Alanine | 25.00 | 25.00 |
| L-Asparagine.$H_2O$ | 28.40 | 28.40 |
| L-Arginine.HCl | 84.00 | 84.00 |
| L-Aspartic acid | 30.00 | 30.00 |
| L-Cystine.2HCl | 91.24 | 91.24 |
| L-Glutamic acid | 75.00 | 75.00 |
| L-Glutamine | 584.00 | 584.00 |
| Glycine | 30.00 | 30.00 |
| L-Histidine.HCl.$H_2O$ | 42.00 | 42.00 |
| L-Isoleucine | 105.00 | 105.00 |
| L-Leucine | 105.00 | 105.00 |
| L-Lysine.HCl | 146.00 | 146.00 |
| L-Methionine | 30.00 | 30.00 |
| L-Phenylalanine | 66.00 | 66.00 |
| L-Proline | 40.00 | 40.00 |
| L-Serine | 42.00 | 42.00 |
| L-Threonine | 95.00 | 95.00 |
| L-Tryptophan | 16.00 | 16.00 |
| L-Tyrosine.2Na.2$H_2O$ | 103.79 | 103.79 |
| L-Valine | 94.00 | 94.00 |
| VITAMINS: | | |
| Biotin | 0.013 | 0.013 |
| D-Ca pantothenate | 4.00 | 4.00 |
| Choline chloride | 4.00 | 4.00 |
| Folic acid | 4.00 | 4.00 |
| i-Inositol | 7.20 | 7.20 |
| Niacinamide | 4.00 | 4.00 |
| Pyridoxal.HCl | 4.00 | 4.00 |
| Riboflavin | 0.40 | 0.40 |
| Thiamine.HCl | 4.00 | 4.00 |
| Vitamin $B_{12}$ | 0.013 | 0.013 |

[1] Dulbecco, R. and Freeman, G. (1959) Virology 8, 396. Smith, J. D., Freeman, G., Vogt, M., and Dulbecco, R. (1960) Virology 12, 185, Tissue Culture Standards Committee, In Vitro 6:2, 93.
[2] Iscove, N. N. and Melchers, F., J. Experimental Medicine 147, 923.
[a] Values shown are in conformance vnth Tissue Culture Standards Committee, In Vitro (1970) 9:6.
[3] Iscove, N. N., personal communication.

| COMPONENT | 320-1885 1X Liquid mg/L | 380-2320 1X Liquid mg/L | 430-1600 Powder mg/L | 320-1965 1X Liquid mg/L | 380-2430 1X Liquid mg/L | 430-2100 Powder mg/L | 430-2800 Powder mg/L | 430-3000 Powder mg/L | 320-1960 1X Liquid mg/L | 320-1970 1X Liquid mg/L | 320-1995 1X Liquid mg/L | 430-3700 Powder mg/L | 320-1968 1X Liquid mg/L | 430-3800 Powder mg/L |
|---|---|---|---|---|---|---|---|---|---|---|---|---|---|---|
| INORGANIC SALTS: | | | | | | | | | | | | | | |
| CaCl$_2$ (anhyd.) | 200.00 | 200.00 | 200.00 | 200.00 | 200.00 | 200.00 | 200.00 | 200.00 | 200.00 | 200.00 | 200.00 | 200.00 | 200.00 | 200.00 |
| Fe(NO$_3$)$_3$.9H$_2$O | 0.10 | 0.10 | 0.10 | 0.10 | 0.10 | 0.10 | 0.10 | 0.10 | 0.10 | 0.10 | 0.10 | 0.10 | 0.10 | 0.10 |
| KCl | 400.00 | 400.00 | 400.00 | 400.00 | 400.00 | 400.00 | 400.00 | 400.00 | 400.00 | 400.00 | 400.00 | 400.00 | 400.00 | 400.00 |
| MgSO$_4$ (anhyd.) | — | — | 97.67 | — | — | 97.67 | 97.67 | 97.67 | — | — | — | 97.67 | — | 97.67 |
| MgSO$_4$.7H$_2$O | 200.00 | 200.00 | — | 200.00 | 200.00 | — | — | — | 200.00 | 200.00 | 200.00 | — | 200.00 | — |
| NaCl | 6400.00 | 4750.00 | 6400.00 | 6400.00 | 4750.00 | 6400.00 | 6400.00 | 6400.00 | 6400.00 | 6400.00 | 6400.00 | 4750.00 | 6400.00 | 6400.00 |
| NaHCO$_3$ | 3700.00 | 3700.00 | — | 3700.00 | 3700.00 | — | — | — | 3700.00 | 3700.00 | 3700.00 | — | 3700.00 | — |
| NaH$_2$PO$_4$.H$_2$O[a] | 125.00 | 125.00 | 125.00 | 125.00 | 125.00 | 125.00 | 125.00 | 125.00 | 125.00 | 125.00 | 125.00 | 125.00 | 125.00 | 125.00 |
| OTHER COMPONENTS: | | | | | | | | | | | | | | |
| D-Glucose | 1000.00 | 1000.00 | 1000.00 | 4500.00 | 4500.00 | 4500.00 | 4500.00 | 4500.00 | 4500.00 | 4500.00 | 4500.00 | 4500.00 | 4500.00 | — |
| Phenol red | 15.00 | 15.00 | 15.00 | 15.00 | 15.00 | 15.00 | 15.00 | — | 15.00 | — | — | 15.00 | 15.00 | — |
| HEPES | — | 5958.00 | — | — | 5958.00 | — | — | — | — | — | — | — | — | — |
| Sodium pyruvate | 110.00 | 110.00 | 110.00 | — | — | — | 110.00 | — | — | — | 110.00 | — | — | — |
| AMINO ACIDS: | | | | | | | | | | | | | | |
| L-Arginine.HCl | 84.00 | 84.00 | 84.00 | 84.00 | 84.00 | 84.00 | 84.00 | 84.00 | 84.00 | 84.00 | 84.00 | 84.00 | 84.00 | 84.00 |
| L-Cystine | 48.00 | 48.00 | — | 48.00 | 48.00 | — | — | — | 48.00 | 48.00 | 48.00 | — | 48.00 | — |
| L-Cystine.2HCl | — | — | 62.57 | — | — | 62.57 | 62.57 | 62.57 | — | — | — | 62.57 | — | 62.57 |
| L-Glutamine | 584.00 | 584.00 | 584.00 | 584.00 | 584.00 | 584.00 | 584.00 | 584.00 | — | — | 584.00 | 584.00 | 584.00 | — |
| Glycine | 30.00 | 30.00 | 30.00 | 30.00 | 30.00 | 30.00 | 30.00 | 30.00 | 30.00 | 30.00 | 30.00 | 30.00 | 30.00 | 30.00 |
| L-Histidine.HCl.H$_2$O | 42.00 | 42.00 | 42.00 | 42.00 | 42.00 | 42.00 | 42.00 | 42.00 | 42.00 | 42.00 | 42.00 | 42.00 | 42.00 | 42.00 |
| L-Isoleucine | 105.00 | 105.00 | 105.00 | 105.00 | 105.00 | 105.00 | 105.00 | 105.00 | 105.00 | 105.00 | 105.00 | 105.00 | 105.00 | 105.00 |
| L-Leucine | 105.00 | 105.00 | 105.00 | 105.00 | 105.00 | 105.00 | 105.00 | 105.00 | 105.00 | 105.00 | 105.00 | 105.00 | 105.00 | 105.00 |
| L-Lysine.HCl | 146.00 | 146.00 | 146.00 | 146.00 | 146.00 | 146.00 | 146.00 | 146.00 | 146.00 | 146.00 | 146.00 | 146.00 | 146.00 | 146.00 |
| L-Methionine | 30.00 | 30.00 | 30.00 | 30.00 | 30.00 | 30.00 | 30.00 | 30.00 | 30.00 | — | 30.00 | 30.00 | 30.00 | 30.00 |
| L-Phenylalanine | 66.00 | 66.00 | 66.00 | 66.00 | 66.00 | 66.00 | 66.00 | 66.00 | 66.00 | 66.00 | 66.00 | 66.00 | 66.00 | 66.00 |
| L-Serine | 42.00 | 42.00 | 42.00 | 42.00 | 42.00 | 42.00 | 42.00 | 42.00 | 42.00 | 42.00 | 42.00 | 42.00 | 42.00 | 42.00 |
| L-Threonine | 95.00 | 95.00 | 95.00 | 95.00 | 95.00 | 95.00 | 95.00 | 95.00 | 95.00 | 95.00 | 95.00 | 95.00 | 95.00 | 95.00 |
| L-Tryptophan | 16.00 | 16.00 | 16.00 | 16.00 | 16.00 | 16.00 | 16.00 | 16.00 | 16.00 | 16.00 | 16.00 | 16.00 | 16.00 | 16.00 |
| L-Tyrosine | 72.00 | 72.00 | — | 72.00 | 72.00 | — | — | — | 72.00 | 72.00 | 72.00 | — | 72.00 | — |
| L-Tyrosine.2Na.2H$_2$O | — | — | 103.79 | — | — | 103.79 | 103.79 | 103.79 | — | — | — | 103.79 | — | 103.79 |
| L-Valine | 94.00 | 94.00 | 94.00 | 94.00 | 94.00 | 94.00 | 94.00 | 94.00 | 94.00 | 94.00 | 94.00 | 94.00 | 94.00 | 94.00 |
| VITAMINS: | | | | | | | | | | | | | | |
| D-Ca pantothenate | 4.00 | 4.00 | 4.00 | 4.00 | 4.00 | 4.00 | 4.00 | 4.00 | 4.00 | 4.00 | 4.00 | 4.00 | 4.00 | 4.00 |
| Choline chloride | 4.00 | 4.00 | 4.00 | 4.00 | 4.00 | 4.00 | 4.00 | 4.00 | 4.00 | 4.00 | 4.00 | 4.00 | 4.00 | 4.00 |
| Folic acid | 4.00 | 4.00 | 4.00 | 4.00 | 4.00 | 4.00 | 4.00 | 4.00 | 4.00 | 4.00 | 4.00 | 4.00 | 4.00 | 4.00 |
| i-Inositol | 7.20 | 7.20 | 7.20 | 7.20 | 7.20 | 7.20 | 7.20 | 7.20 | 7.20 | 7.20 | 7.20 | 7.20 | 7.20 | 7.20 |
| Niacinamide | 4.00 | 4.00 | 4.00 | 4.00 | 4.00 | 4.00 | 4.00 | 4.00 | 4.00 | 4.00 | 4.00 | 4.00 | 4.00 | 4.00 |
| Pyridoxal.HCl | 4.00 | 4.00 | 4.00 | 4.00 | 4.00 | 4.00 | 4.00 | 4.00 | 4.00 | 4.00 | 4.00 | 4.00 | 4.00 | 4.00 |
| Riboflavin | 0.40 | 0.40 | 0.40 | 0.40 | 0.40 | 0.40 | 0.40 | 0.40 | 0.40 | 0.40 | 0.40 | 0.40 | 0.40 | 0.40 |
| Thiamine.HCl | 4.00 | 4.00 | 4.00 | 4.00 | 4.00 | 4.00 | 4.00 | 4.00 | 4.00 | 4.00 | 4.00 | 4.00 | 4.00 | 4.00 |

[1] Dulbecco, R. and Freeman, G. (1959) Virology 8, 396. Smith, J. D., Freeman, G., Vogt, M., and Dulbecco, R. (1960) Virology 12, 185. Tissue Culture Standards Committee, In Vitro 6:2, 93.
[a] Values shown are in conformance with the Tissue Culture Standards Committee, In Vitro (1970) 9:6.

| COMPONENT | 320-2561[2] 1X Liquid mg/L | 410-2000[2] Powder mg/L | 320-2571[2] 1X Liquid mg/L | 410-1900[2] Powder mg/L | 320-2570 1X Liquid mg/L | 320-1090 1X Liquid mg/L | 380-2360 1X Liquid mg/L | 330-1430 10X Liquid mg/L | 410-1700 Powder mg/L | 320-1890 1X Liquid mg/L | 320-1096 1X Liquid mg/L | 410-2400 Powder mg/L | 320-1097 1X Liquid mg/L | 410-2500 Powder mg/L |
|---|---|---|---|---|---|---|---|---|---|---|---|---|---|---|
| INORGANIC SALTS: | | | | | | | | | | | | | | |
| CaCl₂ (anhyd.) | 200.00 | 200.00 | 200.00 | 200.00 | 200.00 | 200.00 | 200.00 | 200.00 | 200.00 | 200.00 | 200.00 | 200.00 | 200.00 | 200.00 |
| KCl | 400.00 | 400.00 | 400.00 | 400.00 | 400.00 | 400.00 | 400.00 | 400.00 | 400.00 | 400.00 | 400.00 | 400.00 | 400.00 | 400.00 |
| MgSO₄ (anhyd.) | — | 97.67 | — | 97.67 | — | — | — | — | 97.67 | — | — | 97.67 | — | 97.67 |
| MgSO₄.7H₂O | 200.00 | — | 200.00 | — | 200.00 | 200.00 | 200.00 | 200.00 | — | 200.00 | 200.00 | — | 200.00 | — |
| NaCl | 6800.00 | 6800.00 | 6800.00 | 6800.00 | 6800.00 | 6800.00 | 6350.00 | 6800.00 | 6800.00 | 6800.00 | 6800.00 | 6800.00 | 6800.00 | 6800.00 |
| NaHCO₃ | 2200.00 | — | 2200.00 | — | 2200.00 | 2200.00 | 2200.00 | — | — | 2200.00 | 1500.00 | — | 2200.00 | — |
| NaH₂PO₄.H₂O[a] | 140.00 | 140.00 | 140.00 | 140.00 | 140.00 | 140.00 | 140.00 | 140.00 | 140.00 | 140.00 | 140.00 | 140.00 | — | — |
| OTHER COMPONENTS: | | | | | | | | | | | | | | |
| D-Glucose | 1000.00 | 1000.00 | 1000.00 | 1000.00 | 1000.00 | 1000.00 | 1000.00 | 1000.00 | 1000.00 | 1000.00 | 1000.00 | 1000.00 | 1000.00 | 1000.00 |
| HEPES | — | — | — | — | — | — | 5958.00 | — | — | — | — | — | — | — |
| Lipoic acid | 0.20 | 0.20 | 0.20 | 0.20 | — | — | — | — | — | — | — | — | — | — |
| Phenol red | 10.00 | 10.00 | 10.00 | 10.00 | 10.00 | 10.00 | 10.00 | 100.00 | 6.00 | 10.00 | 10.00 | 10.00 | 10.00 | 10.00 |
| Sodium pyruvate | 110.00 | 110.00 | 110.00 | 110.00 | — | — | — | — | 100.00 | — | — | — | — | — |
| Sodium succinate | — | — | — | — | — | — | — | — | 75.00 | — | — | — | — | — |
| Succinic acid | — | — | — | — | — | — | — | — | — | — | — | — | — | — |
| AMINO ACIDS: | | | | | | | | | | | | | | |
| L-Alanine | 25.00 | 25.00 | 25.00 | 25.00 | — | — | — | — | — | — | — | — | — | — |
| L-Arginine | 105.00 | — | — | — | — | — | — | — | — | — | — | — | — | — |
| L-Arginine.HCl | — | 126.64 | — | 126.64 | 126.00 | 126.00 | 126.00 | 126.00 | 126.00 | 126.00 | 126.00 | 126.00 | 126.00 | 126.00 |
| L-Asparagine.H₂O | 50.00 | 50.00 | 50.00 | 50.00 | — | — | — | — | — | — | — | — | — | — |
| L-Aspartic acid | 30.00 | 30.00 | 30.00 | 30.00 | — | — | — | — | — | — | — | — | — | — |
| L-Cystine | 24.00 | — | 24.00 | — | 24.00 | 24.00 | 24.00 | 240.00 | — | 24.00 | — | — | 24.00 | — |
| L-Cystine.2HCl | — | 31.28 | — | 31.28 | — | — | — | — | 31.00 | — | 31.00 | 31.29 | — | 31.29 |
| L-Cysteine.HCl.H₂O | 100.00 | 100.00 | 100.00 | 100.00 | — | — | — | — | — | — | — | — | — | — |
| L-Glutamic acid | 75.00 | 75.00 | 75.00 | 75.00 | — | — | — | — | — | — | — | — | — | — |
| L-Glutamine | 292.00 | 292.00 | 292.00 | 292.00 | 292.00 | — | — | — | — | — | — | 292.00 | 292.00 | 292.00 |
| Glycine | 50.00 | 50.00 | 50.00 | 50.00 | — | — | — | — | — | — | — | — | — | — |
| L-Histidine | 31.00 | — | — | — | — | — | — | — | — | — | — | — | — | — |
| L-Histidine.HCl.H₂O | — | 42.00 | 42.00 | 42.00 | 42.00 | 42.00 | 42.00 | 420.00 | 42.00 | 42.00 | 42.00 | 42.00 | 42.00 | 42.00 |
| L-Isoleucine | 52.40 | 52.40 | 52.40 | 52.40 | 52.00 | 52.00 | 52.00 | 520.00 | 52.00 | 52.00 | 52.00 | 52.00 | 52.00 | 52.00 |
| L-Leucine | 52.40 | 52.40 | 52.40 | 52.40 | 52.00 | 52.00 | 52.00 | 520.00 | 52.00 | — | 52.00 | — | 52.00 | 52.00 |
| L-Lysine | 58.00 | — | 58.00 | — | — | — | — | — | — | — | — | — | — | — |
| L-Lysine.HCl | — | 72.50 | — | 72.50 | 72.50 | 72.50 | 72.50 | 725.00 | 72.50 | 72.50 | 72.50 | — | 72.50 | 72.50 |
| L-Methionine | 15.00 | 15.00 | 15.00 | 15.00 | 15.00 | 15.00 | 15.00 | 150.00 | 15.00 | 15.00 | 15.00 | — | 15.00 | 15.00 |
| L-Phenylalanine | 32.00 | 32.00 | 32.00 | 32.00 | 32.00 | 32.00 | 32.00 | 320.00 | 32.00 | 32.00 | 32.00 | 32.00 | 32.00 | 32.00 |
| L-Proline | 40.00 | 40.00 | 40.00 | 40.00 | — | — | — | — | — | — | — | — | — | — |
| L-Serine | 25.00 | 25.00 | 25.00 | 25.00 | — | — | — | — | — | — | — | — | — | — |
| L-Threonine | 48.00 | 48.00 | 48.00 | 48.00 | 48.00 | 48.00 | 48.00 | 480.00 | 48.00 | 48.00 | 48.00 | 48.00 | 48.00 | 48.00 |
| L-Tryptophan | 10.00 | 10.00 | 10.00 | 10.00 | 10.00 | 10.00 | 10.00 | 100.00 | 10.00 | 10.00 | 10.00 | 10.00 | 10.00 | 10.00 |
| L-Tyrosine | 36.00 | — | 36.00 | — | 36.00 | 36.00 | 36.00 | 360.00 | 36.00 | 36.00 | — | — | 36.00 | — |
| L-Tyrosine.2Na.2H₂O | — | 51.90 | — | 51.90 | — | — | — | — | — | — | 51.90 | 51.90 | — | 51.90 |
| D-Valine | — | — | — | — | 92.00 | — | — | — | — | — | — | — | — | — |
| L-Valine | 46.00 | 46.00 | 46.00 | 46.00 | — | 46.00 | 46.00 | 460.00 | 46.00 | 46.00 | 46.00 | 46.00 | 46.00 | 46.00 |
| VITAMINS: | | | | | | | | | | | | | | |
| L-Ascorbic acid | 50.00 | 50.00 | — | 50.00 | — | — | — | — | — | — | — | — | — | — |
| Biotin | 0.10 | 0.10 | — | 0.10 | — | — | — | — | — | — | — | — | — | — |
| D-Ca pantothenate | 1.00 | 1.00 | 1.00 | 1.00 | 1.00 | 1.00 | 1.00 | 10.00 | 1.00 | 1.00 | 1.00 | 1.00 | 1.00 | 1.00 |

-continued

| | | | | | Minimum Essential Media (MEM)[1] | | | | | | | | | |
|---|---|---|---|---|---|---|---|---|---|---|---|---|---|---|
| COMPONENT | 320-2561[2] 1X Liquid mg/L | 410-2000[2] Powder mg/L | 320-2571[2] 1X Liquid mg/L | 410-1900[2] Powder mg/L | 320-2570 1X Liquid mg/L | 320-1090 1X Liquid mg/L | 380-2360 1X Liquid mg/L | 330-1430 10X Liquid mg/L | 410-1700 Powder mg/L | 320-1890 1X Liquid mg/L | 320-1096 1X Liquid mg/L | 410-2400 Powder mg/L | 320-1097 1X Liquid mg/L | 410-2500 Powder mg/L |
| Choline bitartrate | — | — | — | — | — | — | — | — | 1.80 | — | — | — | — | — |
| Choline chloride | 1.00 | 1.00 | 1.00 | 1.00 | 1.00 | 1.00 | 1.00 | 10.00 | 1.00 | 1.00 | 1.00 | 1.00 | 1.00 | 1.00 |
| Folic acid | 1.00 | 1.00 | 1.00 | 1.00 | 1.00 | 1.00 | 1.00 | 10.00 | 1.00 | 1.00 | 1.00 | 1.00 | 1.00 | 1.00 |
| i-Inositol | 2.00 | 2.00 | 2.00 | 2.00 | 2.00 | 2.00 | 2.00 | 20.00 | 2.00 | 2.00 | 2.00 | 2.00 | 2.00 | 2.00 |
| Niacinamide | 1.00 | 1.00 | 1.00 | 1.00 | 1.00 | 1.00 | 1.00 | 10.00 | 1.00 | 1.00 | 1.00 | 1.00 | 1.00 | 1.00 |
| Pyridoxal.HCl | 1.00 | 1.00 | 1.00 | 1.00 | 1.00 | 1.00 | 1.00 | 10.00 | 1.00 | 1.00 | 1.00 | 1.00 | 1.00 | 1.00 |
| Riboflavin | 0.10 | 0.10 | 0.10 | 0.10 | 0.10 | 0.10 | 0.10 | 1.00 | 0.10 | 0.10 | 0.10 | 0.10 | 0.10 | 0.10 |
| Thiamine.HCl | 1.00 | 1.00 | 1.00 | 1.00 | 1.00 | 1.00 | 1.00 | 10.00 | 1.00 | 1.00 | 1.00 | 1.00 | 1.00 | 1.00 |
| Vitamin B12 | 1.36 | 1.36 | 1.36 | 1.36 | — | — | — | — | — | — | — | — | — | — |
| RIBONUCLEOSIDES: | | | | | | | | | | | | | | |
| Adenosine | — | — | 10.00 | 10.00 | — | — | — | — | — | — | — | — | — | — |
| Cytidine | — | — | 10.00 | 10.00 | — | — | — | — | — | — | — | — | — | — |
| Guanosine | — | — | 10.00 | 10.00 | — | — | — | — | — | — | — | — | — | — |
| Uridine | — | — | 10.00 | 10.00 | — | — | — | — | — | — | — | — | — | — |
| DEOXYRIBONUCLEOSIDES | | | | | | | | | | | | | | |
| 2' Deoxyadenosine | — | — | 10.00 | 10.00 | — | — | — | — | — | — | — | — | — | — |
| 2' Deoxycytidine.HCl | — | — | 11.00 | 11.00 | — | — | — | — | — | — | — | — | — | — |
| 2' Deoxyguanosine | — | — | 10.00 | 10.00 | — | — | — | — | — | — | — | — | — | — |
| Thymidine | — | — | 10.00 | 10.00 | — | — | — | — | — | — | — | — | — | — |

[1]Eagle, H. (1959) Science, 130, 432.
[2]Nature, New Biology (1971) 230, 310.
[a]Original formula lists this component as NaH$_2$PO$_4$.2H$_2$O.

| RPMI Media 1640[1] | | | | | | | | | |
|---|---|---|---|---|---|---|---|---|---|
| | COMPONENT | | | | | | | | |
| | 320-1870 1X Liquid mg/L | 320-1875 1X Liquid mg/L | 330-2511 10X Liquid mg/L | 380-2400 1X Liquid mg/L | 430-1800 Powder mg/L | 430-3200 Powder mg/L | 430-3400 powder mg/L | 320-1835 1X Liquid mg/L | 320-1877 1X Liquid mg/L |
| INORGANIC SALTS: | | | | | | | | | |
| Ca(NO$_3$)$_2$.4H$_2$O | 100.00 | 100.00 | 1000.00 | 100.00 | 100.00 | 100.00 | 100.00 | 100.00 | 100.00 |
| KCl | 400.00 | 400.00 | 4000.00 | 400.00 | 400.00 | 400.00 | 400.00 | 400.00 | 400.00 |
| MgSO$_4$ (anhyd.) | — | — | — | — | 48.84 | 48.84 | 48.84 | — | — |
| MgSO$_4$.7H$_2$O | 100.00 | 100.00 | 1000.00 | 100.00 | — | — | — | 100.00 | 100.00 |
| NaCl | 6000.00 | 6000.00 | 60000.00 | 5300.00 | 6000.00 | 6000.00 | 5850.00 | 6000.00 | 6000.00 |
| NaHCO$_3$ | 2000.00 | 2000.00 | — | 2000.00 | — | — | — | 2000.00 | 2000.00 |
| Na$_2$HPO$_4$ (anhyd.) | — | — | — | — | 800.00 | 800.00 | 800.00 | — | — |
| Na$_2$HPO$_4$.7H$_2$O | 1512.00 | 1512.00 | 15120.00 | 1512.00 | — | — | — | 1512.00 | — |
| OTHER COMPONENTS: | | | | | | | | | |
| D-Glucose | 2000.00 | 2000.00 | 20000.00 | 2000.00 | 2000.00 | 2000.00 | 2000.00 | 2000.00 | 2000.00 |
| Glutathione (reduced) | 1.00 | 1.00 | 10.00 | 1.00 | 1.00 | 1.00 | 1.00 | 1.00 | 1.00 |
| HEPES | — | — | — | 5958.00 | — | — | 5957.50 | — | — |
| Phenol red | 5.00 | 5.00 | 50.00 | 5.00 | 5.00 | — | 5.00 | — | 5.00 |
| AMINO ACIDS: | | | | | | | | | |
| L-Arginine | 200.00 | 200.00 | 2000.00 | 200.00 | 200.00 | 200.00 | 200.00 | 200.00 | 200.00 |
| L-Asparagine | 50.00 | 50.00 | 500.00 | 50.00 | 50.00 | 50.00 | 50.00 | 50.00 | 50.00 |
| L-Aspartic acid | 20.00 | 20.00 | 200.00 | 20.00 | 20.00 | 20.00 | 20.00 | 20.00 | 20.00 |
| L-Cystine | 50.00 | 50.00 | 500.00 | 50.00 | — | — | — | 50.00 | 50.00 |
| L-Cystine.2HCl | — | — | — | — | 65.15 | 65.15 | 65.15 | — | — |
| L-Glutamic acid | 20.00 | 20.00 | 200.00 | 20.00 | 20.00 | 20.00 | 20.00 | 20.00 | 20.00 |
| L-Glutamine | — | 300.00 | 3000.00 | 300.00 | 300.00 | 300.00 | 300.00 | 300.00 | 300.00 |
| Glycine | 10.00 | 10.00 | 100.00 | 10.00 | 10.00 | 10.00 | 10.00 | 10.00 | 10.00 |
| L-Histidine | 15.00 | 15.00 | 150.00 | 15.00 | 15.00 | 15.00 | 15.00 | 15.00 | 15.00 |
| L-Hydroxyproline | 20.00 | 20.00 | 200.00 | 20.00 | 20.00 | 20.00 | 20.00 | 20.00 | 20.00 |
| L-Isoleucine | 50.00 | 50.00 | 500.00 | 50.00 | 50.00 | 50.00 | 50.00 | 50.00 | 50.00 |
| L-Leucine | 50.00 | 50.00 | 500.00 | 50.00 | 50.00 | 50.00 | 50.00 | 50.00 | 50.00 |
| L-Lysine.HCl | 40.00 | 40.00 | 400.00 | 40.00 | 40.00 | 40.00 | 40.00 | 40.00 | 40.00 |
| L-Methionine | 15.00 | 15.00 | 150.00 | 15.00 | 15.00 | 15.00 | 15.00 | 15.00 | 15.00 |
| L-Phenylalanine | 15.00 | 15.00 | 150.00 | 15.00 | 15.00 | 15.00 | 15.00 | 15.00 | 15.00 |
| L-Proline | 20.00 | 20.00 | 200.00 | 20.00 | 20.00 | 20.00 | 20.00 | 20.00 | 20.00 |
| L-Serine | 30.00 | 30.00 | 300.00 | 30.00 | 30.00 | 30.00 | 30.00 | 30.00 | 30.00 |
| L-Threonine | 20.00 | 20.00 | 200.00 | 20.00 | 20.00 | 20.00 | 20.00 | 20.00 | 20.00 |
| L-Tryptophan | 5.00 | 5.00 | 50.00 | 5.00 | 5.00 | 5.00 | 5.00 | 5.00 | 5.00 |
| L-Tyrosine | 20.00 | 20.00 | 200.00 | 20.00 | — | — | — | 20.00 | 20.00 |
| L-Tyrosine.2Na.2H$_2$O | — | — | — | — | 28.83 | 28.83 | 28.83 | — | — |
| L-Valine | 20.00 | 20.00 | 200.00 | 20.00 | 20.00 | 20.00 | 20.00 | 20.00 | 20.00 |
| VITAMINS: | | | | | | | | | |
| Biotin | 0.20 | 0.20 | 2.00 | 0.20 | 0.20 | 0.20 | 0.20 | 0.20 | 0.20 |
| D-Ca pantothenate | 0.25 | 0.25 | 2.50 | 0.25 | 0.25 | 0.25 | 0.25 | 0.25 | 0.25 |
| Choline chloride | 3.00 | 3.00 | 30.00 | 3.00 | 3.00 | 3.00 | 3.00 | 3.00 | 3.00 |
| Folic acid | 1.00 | 1.00 | 10.00 | 1.00 | 1.00 | 1.00 | 1.00 | 1.00 | 1.00 |
| i-Inositol | 35.00 | 35.00 | 350.00 | 35.00 | 35.00 | 35.00 | 35.00 | 35.00 | 35.00 |
| Niacinamide | 1.00 | 1.00 | 10.00 | 1.00 | 1.00 | 1.00 | 1.00 | 1.00 | 1.00 |
| Para-aminobenzoic acid | 1.00 | 1.00 | 10.00 | 1.00 | 1.00 | 1.00 | 1.00 | 1.00 | 1.00 |
| Pyridoxine.HCl | 1.00 | 1.00 | 10.00 | 1.00 | 1.00 | 1.00 | 1.00 | 1.00 | 1.00 |
| Riboflavin | 0.20 | 0.20 | 2.00 | 0.20 | 0.20 | 0.20 | 0.20 | 0.20 | 0.20 |
| Thiamine.HCl | 1.00 | 1.00 | 10.00 | 1.00 | 1.00 | 1.00 | 1.00 | 1.00 | 1.00 |
| Vitamin B$_{12}$ | 0.005 | 0.005 | 0.05 | 0.005 | 0.005 | 0.005 | 0.005 | 0.005 | 0.005 |

[1]Moore, G. E., Gerner, R. E., and Franklin, H. A. (1967) J.A.M.A. 199, 519.

| McCoy's 5A Media (modified)[1,2,3] | | | | | | | | |
|---|---|---|---|---|---|---|---|---|
| | COMPONENT | | | | | | | |
| | 320-6600 1X Liquid mg/L | 380-2330 1X Liquid mg/L | 430-1500 Powder mg/L | 320-6608 1X Liquid mg/L | 320-6601[4] 1X Liquid mg/L | 320-6610 1X Liquid mg/L | 320-6620 1X Liquid mg/L | 320-6630 1X Liquid mg/L |
| INORGANIC SALTS: | | | | | | | | |
| CaCl$_2$ (anhyd.) | 100.00 | 100.00 | 100.00 | — | 140.00 | 100.00 | 100.00 | 100.00 |
| KCl | 400.00 | 400.00 | 400.00 | 400.00 | 400.00 | 400.00 | 400.00 | 400.00 |
| KH$_2$PO$_4$ | — | — | — | — | 60.00 | — | — | — |
| MgCl$_2$.6H$_2$O | — | — | — | — | 100.00 | — | — | — |
| MgSO$_4$ (anhyd.) | — | — | 97.67 | — | — | — | — | — |
| MgSO$_4$.7H$_2$O | 200.00 | 200.00 | — | 200.00 | 100.00 | 200.00 | 200.00 | 200.00 |
| NaCl | 6460.00 | 5100.00 | 6460.00 | 6460.00 | 8000.00 | 6460.00 | 6460.00 | 6460.00 |
| NaHCO$_3$ | 2200.00 | 2200.00 | — | 2200.00 | 350.00 | 2200.00 | 2200.00 | 2200.00 |
| NaH$_2$PO$_4$.H$_2$O | 580.00 | 580.00 | 580.00 | 1400.00 | — | 580.00 | 580.00 | 580.00 |
| Na$_2$HPO$_4$.7H$_2$O | — | — | — | — | 90.00 | — | — | — |
| OTHER COMPONENTS: | | | | | | | | |
| Bacto-peptone | 600.00 | 600.00 | 600.00 | 600.00 | 600.00 | 600.00 | 600.00 | 600.00 |
| Fetal Bovine Serum | — | — | — | — | — | c | c | c |
| D-Glucose | 3000.00 | 3000.00 | 3000.00 | 3000.00 | 1000.00 | 3000.00 | 3000.00 | 3000.00 |

-continued

| McCoy's 5A Media (modified)[1,2,3] | | | | | | | | |
|---|---|---|---|---|---|---|---|---|
| COMPONENT | | | | | | | | |
| | 320-6600 1X Liquid mg/L | 380-2330 1X Liquid mg/L | 430-1500 Powder mg/L | 320-6608 1X Liquid mg/L | 320-6601[4] 1X Liquid mg/L | 320-6610 1X Liquid mg/L | 320-6620 1X Liquid mg/L | 320-6630 1X Liquid mg/L |
| Glutathione (reduced) | 0.50 | 0.50 | 0.50 | 0.50 | 0.50 | 0.50 | 0.50 | 0.50 |
| HEPES | — | 5958.00 | — | — | — | — | — | — |
| Phenol red | 10.00 | 10.00 | 10.00 | 10.00 | 10.00 | 10.00 | 10.00 | 10.00 |
| AMINO ACIDS: | | | | | | | | |
| L-Alanine | 13.90 | 13.90 | 13.90 | 13.90 | 13.90 | 13.90 | 13.90 | 13.90 |
| L-Arginine.HCl | 42.10 | 42.10 | 42.10 | 42.10 | 42.10 | 42.10 | 42.10 | 42.10 |
| L-Asparagine[a] | 45.00 | 45.00 | 45.00 | 45.00 | 45.00 | 45.00 | 45.00 | 45.00 |
| L-Aspartic acid | 19.97 | 19.97 | 19.97 | 19.97 | 19.97 | 19.97 | 19.97 | 19.97 |
| L-Cysteine[b] | 31.50 | 31.50 | 31.50 | 31.50 | 31.50 | 31.50 | 31.50 | 31.50 |
| L-Glutamic acid | 22.10 | 22.10 | 22.10 | 22.10 | 22.10 | 22.10 | 22.10 | 22.10 |
| L-Glutamine | 219.20 | 219.20 | 219.20 | 219.20 | 219.20 | 219.20 | 219.20 | 219.20 |
| Glycine | 7.50 | 7.50 | 7.50 | 7.50 | 7.50 | 7.50 | 7.50 | 7.50 |
| L-Histidine.HCl.H$_2$O | 20.96 | 20.96 | 20.96 | 20.96 | 20.96 | 20.96 | 20.96 | 20.96 |
| L-Hydroxyproline | 19.70 | 19.70 | 19.70 | 19.70 | 19.70 | 19.70 | 19.70 | 19.70 |
| L-Isoleucine | 39.36 | 39.36 | 39.36 | 39.36 | 39.36 | 39.36 | 39.36 | 39.36 |
| L-Leucine | 39.36 | 39.36 | 39.36 | 39.36 | 39.36 | 39.36 | 39.36 | 39.36 |
| L-Lysine.HCl | 36.50 | 36.50 | 36.50 | 36.50 | 36.50 | 36.50 | 36.50 | 36.50 |
| L-Methionine | 14.90 | 14.90 | 14.90 | 14.90 | 14.90 | 14.90 | 14.90 | 14.90 |
| L-Phenylalanine | 16.50 | 16.50 | 16.50 | 16.50 | 16.50 | 16.50 | 16.50 | 16.50 |
| L-Proline | 17.30 | 17.30 | 17.30 | 17.30 | 17.30 | 17.30 | 17.30 | 17.30 |
| L-Serine | 26.30 | 26.30 | 26.30 | 26.30 | 26.30 | 26.30 | 26.30 | 26.30 |
| L-Threonine | 17.90 | 17.90 | 17.90 | 17.90 | 17.90 | 17.90 | 17.90 | 17.90 |
| L-Tryptophan | 3.10 | 3.10 | 3.10 | 3.10 | 3.10 | 3.10 | 3.10 | 3.10 |
| L-Tyrosine | 18.10 | 18.10 | — | 18.10 | 18.10 | 18.10 | 18.10 | 18.10 |
| L-Tyrosine.2Na.2H$_2$O | — | — | 26.10 | — | — | — | — | — |
| L-Valine | 17.60 | 17.60 | 17.60 | 17.60 | 17.60 | 17.60 | 17.60 | 17.60 |
| VITAMINS: | | | | | | | | |
| Ascorbic acid | 0.50 | 0.50 | 0.50 | 0.50 | 0.50 | 0.50 | 0.50 | 0.50 |
| Biotin | 0.20 | 0.20 | 0.20 | 0.20 | 0.20 | 0.20 | 0.20 | 0.20 |
| Choline chloride | 5.00 | 5.00 | 5.00 | 5.00 | 5.00 | 5.00 | 5.00 | 5.00 |
| D-Ca pantothenate | 0.20 | 0.20 | 0.20 | 0.20 | 0.20 | 0.20 | 0.20 | 0.20 |
| Folic acid | 10.00 | 10.00 | 10.00 | 10.00 | 10.00 | 10.00 | 10.00 | 10.00 |
| i-Inositol | 36.00 | 36.00 | 36.00 | 36.00 | 36.00 | 36.00 | 36.00 | 36.00 |
| Niacinamide | 0.50 | 0.50 | 0.50 | 0.50 | 0.50 | 0.50 | 0.50 | 0.50 |
| Nicotinic acid | 0.50 | 0.50 | 0.50 | 0.50 | 0.50 | 0.50 | 0.50 | 0.50 |
| Para-aminobenzoic acid | 1.00 | 1.00 | 1.00 | 1.00 | 1.00 | 1.00 | 1.00 | 1.00 |
| Pyridoxal.HCl | 0.50 | 0.50 | 0.50 | 0.50 | 0.50 | 0.50 | 0.50 | 0.50 |
| Pyridoxine.HCl | 0.50 | 0.50 | 0.50 | 0.50 | 0.50 | 0.50 | 0.50 | 0.50 |
| Riboflavin | 0.20 | 0.20 | 0.20 | 0.20 | 0.20 | 0.20 | 0.20 | 0.20 |
| Thiamine.HCl | 0.20 | 0.20 | 0.20 | 0.20 | 0.20 | 0.20 | 0.20 | 0.20 |
| Vitamin B$_{12}$ | 2.00 | 2.00 | 2.00 | 2.00 | 2.00 | 2.00 | 2.00 | 2.00 |

[1] McCoy, T. A., Maxwell, M., and Kruse, P. F. (1959) Proc. Soc. Exper. Biol. Med. 100, 115.
[2] Hsu, T. C. and Kellogg, D. S., Jr. (1960) J. Nat. Cancer Inst. 25, 221.
[3] Iwakata, S. and Grace, J. T., Jr. (1964) N.Y.J. Med. 64:18, 2279.
[4] McCoy's 5A Medium formulated with Hanks' and Suspension Salts is a GIBCO modification and is not cited in references 1-3.
[a] HCl form listed by the Tissue Culture Standards Committee, In Vitro (1974) 9:6.
[b] Monohydrate form listed by the Tissue Culture Standards Committee, In Vitro (1974) 9:6.
[c] Fetal Bovine Serum Supplementation:

| Cat. No. | FBS |
|---|---|
| 320-6610 | 10% v/v |
| 320-6620 | 20% v/v |
| 320-6630 | 30% v/v |

The serum component may be present in the culture in an amount of at least 1% (v/v) to 50% (v/v). The serum concentration may be preferably in the neighborhood of 15 to 30% (v/v). For higher serum concentrations, the exchange rate is increased proportionately. The third component may be present in an amount of from $10^{-7}$ M to $10^{-4}$ M, and is preferably present in an amount of from $5 \times 10^{-6}$ to $5 \times 10^{-5}$ M. The media component represents the balance such that all three components add up to 100%. Alternatively the serum component can be replaced by any of several standard serum replacement mixtures which typically include insulin, albumin, and lecithin or cholesterol. See, Migliaccio et al, Exp. Hematol. (1990) 18:1049–1055, Iscove et al, Exp. Cell Res. (1980) 126:121–126, and Dainiak et al, J. Clin. Invest. (1985) 76:1237–1242.

Illustratively, human hematopoietic stem cell concentration may be increased as follows. Red blood cells are removed from a bone marrow aspirate by ficol-hypaque gradient centriguration. The mononuclear cells are then incubated with a "cocktail" of antibodies which recognize mature blood elements including red blood cells and red blood cell, granulocytes, macrophages, and mature lymphocytes (both B- and T-cells). In addition, antibodies are included which recognize committed progenitor cells (including anti CD 33). The mature cells are then removed by one of various procedures including panning, magnetic beads, or cell sorting on a Fluorescent Activated Cell Sorter (FACS). By removing the mature elements, the chance of recombinant virus infection, and therefore transfer of the desired gene(s), to hematopoietic stem cells is greatly facilitated.

Having generally described this invention, a further understanding can be obtained by reference to certain specific examples which are provided herein for purposes of illustration only and are not intended to be limiting unless otherwise specified.

ILLUSTRATIVE CELL SEPARATION AND STAINING PROCEDURES

Separation of Bone Marrow Cells on Ficoll

1. Dilute the bone marrow sample at a 1:4 ratio in I-MDM kept at room temperature (Iscove's Modified Dulbecco Medium; GIBCO; Cat. No. 430-2200).
2. Carefully, layer 35 ml of the diluted bone marrow sample onto 15 ml of Ficoll-Paque at room temp. (Sp. Gr. 1.077 g/cc; Pharmacia; Cat. No. 17-0840-02) in 50 ml centrifuge tube.
3. Centrifuge at 700×g (1800 rpm on Beckman) for 30 min. at room temperature (20° C.).
4. After centrifugation remove most of the upper layer (leaving about 5 ml above interphase), collect the interphase layer (bone marrow cells), and wash 3 times in ice cold I-MDM according to the following:
   First wash: 1400 rpm/15 min/4° C.
   Second wash: 1200 rpm/10 min/4° C.
   Third wash: 1200 rpm/10 rpm/4° C.
5. After the third wash the cells are suspended either in media or a balanced salt solution etc... (depending on whtat is to be done with them), and counted after making a 1:10 dilution of the cells in acetic acid (10 μl cell suspension=90 μl of 2% acetic acid in PBS; this will allow for counting WBCs only, since RBCs get lysed in the acetic acid).
6. Cells are then suspended to the desired final concentration in the appropriate medium (for media refer to the different applications).

Fluorescent Staining for MY-10 Positive Bone Marrow Cells

Reagents

| Standard Buffer: | |
|---|---|
| Powdered Bacto Dried DIFCO Buffer (Baxter; Cat. No. 2314-15GB): | 200 g |
| 10% NaN$_3$ (sodium azide): | 20 g |
| Heat inactivated fetal calf serum (56° C., 30 min.) | 200 ml |
| Bring volume to 20 liters in dd-H$_2$O; pH 7.15-7.25; store at 42 C. | |
| Good for 1 month | |
| 2% Paraformaldehyde solution | |
| paraformaldehyde: | 10 g |
| dd-H$_2$O: | 500 ml |
| 10N NaOH (under the hood) | 8-20 drops |
| powdered Bacto dried Difco Buffer | 5 g |

Pour dd-H$_2$O in 500 ml flask and stir on a hot plate to 60° C. in the hood.
Add 10 gr. parafromaldehyde
Add NaOH dropwise until solution clears
Add 5 gr DIFCO
Let cool, Adjust pH to 7.35-7.45 with 2 N HCl.

1. After counting the cells, they are washed once in standard buffer (100 rpm, 5 min. 4° C.).
2. Cells are then suspended in standard buffer at the concentration of $2 \times 10^5$ cells/ml.
3. Two 50 μl aliquots of the cells are deposited into 2 15 ml centrifuge tubes.
4. To one tube 50 μl of a 1:5 dilution of anti-HPCA-1 are added (anti-human progenitor cell antigen; Becton Dickinson; Cat. No. 7660; diluted 1:5 in standard buffer). To the other tube, 50 μl of a 1:5 dilution of MIg are added (Mouse IgG1 control; Becton Dickinson; Cat. No. 9040; diluted 1:5 in standard buffer).
5. Both tubes are then incubated for ½ hour on ice.
6. After incubation; cells are washed twice in 5 ml standard buffer (1000 rpm, 5 min, 4° C.).
7. After the second wash, cell pellets are resuspended in 50 μl of a 1:40 dilution of GAM-FITC (Affinity isolated Goat F(ab')2 anti-mouse IgG and IgM, human Ig adsorbed, Fluorescein conjugated; TAGO; Cat. No. 4353; diluted 1:40 in standard buffer).
8. Cells are incubated for ½ and hour in the dark, on ice.
9. After incubation, cells are washed twice in 5 ml standard buffer (100 rpm, 5 min., 4° C.), and each of the pellets is resuspended in 100 μ standard buffer plus 100 μl 2% paraformaldehyde solution.
10. Cells are then analyzed for fluorescence using the flow cytometer. Percent positive fluorescence constitute % fluorescence in anti-HPCA-1 sample minus % fluorescence in MIg sample.

Fluorescent Staining of Bone Marrow Cells to Sort Out Mature Progenitor Cells Objectives:
The purpose of this staining is to enrich for hematopoietic stem cells (most primitve stem cells) by removing mature cell populations, using the flow cytometer or magnetic beads. It is always a good idea to retain some cells as total bone marrow cells (after Ficoll separation) to stain for MY-10 positive cells in order to compare with the outcome of sorting and determine extent of enrichment.

1. Cells are separated on Ficoll-Paque as described before. (Remove $0.5 \times 10^6$ cells and divide into 2 portions to stain with anti-HPCA-1/GAM-FITC and MIg/GAM-FITC).
2. After the third wash the cell pellet is suspended in the monoclonal antibody cocktail (refer to section describing the making of this cocktail) using 1 ml of the cocktail per $10^7$ cells, and cells are incubated on ice for 1 hour.
3. Cells are then washed three times in excess ice cold I-MDM (1000 rpm, 5 min, 4° C.).
4. After the third wash cells are suspended in a 1:40 dilution of GAM-FITC (diluted in I-MDM, not standard buffer) at the rate of 50 μl per $0.25 \times 10^6$ cells, and incubated on ice in the dark for ½ an hour.
5. After incubation, cells are washed three times in ice cold I-MDM, and after the final wash they are suspended in 2-4 ml of ice cold I-MDM and kept on ice until sorting.
6. Cells are then sorted on the flow cytometer based on fluorescence, to eclude the upper 85% of the fluorescence histogram. Sorting could be repeated twice for better enrichment.
7. After sorting, cells are counted, washed, and an aliquot is stained for MY-10 positive cells (as described above) to determine the extent of enrichment in comparison to stained aliquots of the total bone marrow cells.

Selecting for Immature Cells by Using Magnetic Antibodies

1. Follow steps 1-3 in the procedure for Fluorescent staining of bone marrow cells to sort out mature cells. Note: sodium azide is not included in any of the buffers.
2. In the meantime wash an appropriate amount of magnetic goat anti-mouse Ig (Biomag; Collaborative Research; Cat. No. 74340-50; 1 mg/ml; $5 \times 10^8$ particles/ml) 3 times in ice cold I-MDM at 1500 rpm, 5 min.

4° C. (to wash off the sodium azide which is used as a preservative).

3. Resuspend the cell pellet obtained after the third wash in "step 1" in Biomag at the rate of 50 particles Biomag/cell (e.g., for $1 \times 10^6$ cells use $5 \times 10^7$ particles, therefore, 0.1 ml of Biomag).

4. Deposit the cells in a T-25 or T-75 tissue culture flask (depending on cell numbers) and incubate on ice for ½ hour with intermittent shaking.

5. After incubation, lay the flask onto the flat magnet (provided with the Biomag), secure with a rubber band or tape, and incubate at 4° C. for 10–15 min.

6. Stand the magnet and the flask into an upright position and collect the supernatent.

7. Repeat steps 4–6 two more times.

8. Count the cells, wash once in ice cold I-MDM, remove an aliquot to stain for MY-10 positive, and resuspend in appropriate media for further use.

I. Medium Replacement

Materials and Methods

Cells: Human bone marrow cells were obtained from heparinized aspirates from the iliac crest of informed and consenting individuals. The bone marrow was separated by a Ficoll-Paque (Pharmacia, No. 17-0840-02) density gradient centrifugation and the low density cells ($<1.077$ gm/cm$^3$) were collected and washed 3 times with Iscove's Modified Dulbecco's Medium (IMDM). The cells were counted between the second and third washes. The cells were then seeded onto 24-well tissue culture plates (Costar ND. 3524) in duplicate or triplicate at 1, 2, and $5 \cdot 10^6$ cells/ml at 322 μl/well.

Long-term culture conditions: The low density cells were incubated in IMDM supplemented with 10% fetal calf serum (Hyclone Laboratories, 10% horse serum (Hyclone Laboratories), 1% penicillin/streptomycin (Sigma, 10,000 U/ml penicillin G and 10 mg/ml streptomycin, Cat. No. P3539), and $10^{-5}$ M hydrocortisone (17-Hydroxy-corticosterone, Sigma, Cat. No. H0888) in a humidified 5% $CO_2$/95% air atmosphere. The cultures were treated with one of three medium exchange schedules, 100% daily medium exchange (7/wk), 50% daily medium exchange (3.5/wk), or 50% biweekly medium exchange (1/wk). Twice per week during the medium exchange, 50% of the nonadherent cells were removed from each culture well and counted using a hemocytometer.

When the cells were removed for counting (twice/week), all of the medium removed during feeding of the 3.5/wk and 1/wk cultures was saved for cell counts and fresh medium returned to the wells. The 7/wk cultures required saving ½ of the removed medium for cell counts, while centrifuging and returning the non-adherent cells in the remaining ½ of the medium removed. Fresh medium was then added to each well to replace the medium removed for cell counts. On days when the cells were not removed for counting, 100% or 50% of the medium was removed from each of the 7/wk and 3.5/wk culture wells respectively, the cells were centrifuged and returned to the original wells with additional fresh medium.

Methylcellulose and morphologic assays: One every other week the non-adherent cells removed for cell counts were plated in methylcellulose in the presence of erythropoietin, GM-CSF, and IL-3, and the Granulocyte Macrophase-Colony Forming Units (CFU-GM) were enumerated. Aliquot of removed cells were cytocentrifuged, stained with Wright-Giemsa, and differential cell counts performed.

Statistical analysis: The biweekly cell production results are expressed as the mean ±SEM from replicate cultures. The probability of significant differences between groups of cultures was determined by comparing the normalized cumulative cell production values from the rapidly exchanged cultures (7/wk and 3.5/wk) to the matched control cultures (1/wk) using a paired t-test. Statistical significance was taken at the 5% level.

Results

Kinetics of nonadherent cell production: Nonadherent cell production was examined both as a function of inoculum cell density (over the range $1-5 \cdot 10^6$ cells/ml) and medium exchange rate. The medium exchange rate was varied from one medium volume exchange per week, the traditional Dexter culture rate, to seven medium volume exchanges per week. The biweekly number of cells collected was normalized by dividing by the number of cell inoculated per culture.

At each medium exchange rate, the normalized cell collection curves did not change significantly with inoculum density. The cell production for the cultures maintained at the three medium perfusion rates of 7/wk, 3.5/wk and 1/wk were similar when normalized to the number of cells inoculated per culture. Comparison of the final cumulative cell productions between inoculum densities showed no significant differences, at any of the three medium exchange rates ($p > 0.20$ by a paired t-test for all pairs of samples).

The medium exchange rate, in contrast, strongly influenced the rate and longevity of cell production in these cultures. Cell production of the cultures exchanged at 1/wk (control), 3.5/wk, and 7/wk all decayed over the first few weeks. Differences in culture productivity, however, became apparent after week 3 in culture. Between weeks 3 to 10, the cell production was constant in the 7/wk cultures, constant at a lower level in the 1/wk cultures, but increased exponentially in the 3.5/wk cultures. After weeks 10 to 12, cell production declined in all cultures until culture termination.

Results for the 1/wk exchanged cultures are equivalent to those commonly observed in traditional human Dexter cultures in a variety of systems, whereas the rapidly exchanged cultures of 3.5 and 7/wk showed increased cell productivity when compared to previous optimum culture methods. Cultures in which ½ of the medium was exchanged daily (3.5/wk) maintained increased cell production for substantially longed than either the control (1/wk) or complete daily exchange (7/wk) cultures. Between weeks 3 and 9, the number of nonadherent cells collected from the 3.5/wk exchanged cultures increased exponentially with a doubling every 2.1 weeks.

The cell production under the 3.5/wk and 1/wk protocols can be directly compared by plotting the cell production under the 3.5/wk exchange rate as a percentage of the production of the cultures with an exchange rate of 1/wk. This comparison shows that during the initial decay phase the cell production under the two protocols is similar. However, between weeks 3.5 and 18, the cell production under the 3.5/wk exchange rate is consistently higher.

The proliferative potential of the cultures can thus be measured by their ability to produce cells following the initial decay. The normalized cumulative cell production following week 3 ($\Sigma_{i=7}^{n}$, $C_i/C_o$ was independent of the cell inoculation density for the medium exchange rates of 7/wk, 3.5/wk. Cell production data from the cultures at similar medium exchange rates were qualitatively and statistically similar, and were therefore density averaged and combined (bottom panel) to obtain a larger statistical sample. The density averaged cumulative cell production between weeks 3.5 and 20 was: 0.22 for the 7/wk; 0.40 for the 3.5/wk; and 0.15 for the 1/wk cultures. The increase in the medium exchange rate from 1/wk to 7/wk thus increased the cell production about 60% over the typical Dexter culture medium exchange schedule. The 3.5/wk exchange rate resulted in almost 3-fold cumulative cell production increase compared to the 1/wk Dexter protocol. Statistical analysis of these data using a paired t-test, demonstrated significant differences between both the 7/wk vs. 1/wk and the 3.5/wk vs. 1/wk at the 5% level of significance. The medium exchange rate of 3.5/wk thus improves the cell production rate over the traditional Dexter protocol of 1/wk.

Granulocyte-macrophase progenitor cell production: Granulocyte-macrophase progenitor cell assays were performed from replicates of a given medium perfusion as it is an indirect measure of stem cell renewal. Progenitor cells can only be present after several weeks in culture by differentiation from an earlier cell, presumably a stem cell, which is still present in culture. Thus, these data suggest that more physiologic, rapid medium/serum exchange rate and higher cell densities may have provided conditions that supported some degree of stem cell renewal for five months.

Nonadherent cell morphology: To determine whether the prolonged hematopoiesis supported by the 3.5/wk cultures was qualitatively different from the other cultures, the nonadherent cells collected between weeks 10 and 19 were stained and typed morphologically. At the exchange rates of 1/wk and 7/wk, the cells produced were mostly macrophages by week 15 and thereafter (Table 3), which is similar to results from studies in other laboratories. In contrast, the cultures perfused at a rate of 3.5 medium volumes per week and seeded at $5 \cdot 10^6$ cells/ml produced granulocytes as well as macrophages through week 19. Thus, it seems that this medium exchange rate and inoculum density more effectively reconstituted granulopoiesis in vitro.

TABLE 2

The average number of nonadherent progenitor cells removed from long term bone marrow cultures (LTBMCs) as a function of the medium perfusion rate and inoculum density.

| Week | 7/wk | | | 3.5/wk | | | 1/wk | | |
|---|---|---|---|---|---|---|---|---|---|
| | $5 \times 10^6$ per ml | $2 \times 10^6$ per ml | $1 \times 10^6$ per ml | $5 \times 10^6$ per ml | $2 \times 10^6$ per ml | $1 \times 10^6$ per ml | $5 \times 10^6$ per ml | $2 \times 10^6$ per ml | $1 \times 10^6$ per ml |
| 2 | 237 ± 27 | 11 ± 3.3 | 106 ± 5 | 120 ± 16 | 132 ± 7.9 | 167 ± 13 | 368 ± 29 | 94 ± 20.8 | 335 ± 46 |
| 4 | 149 ± 21 | 101 ± 5.1 | 104 ± 10 | 93 ± 10 | 37 ± 5.6 | 20 ± 0 | 21 ± 1.3 | 2 ± 0 | 8 ± 4.4 |
| 6 | 47.7 ± 7 | 12 ± 2.5 | 8 ± 0 | 17 ± 3 | 6 ± 4.1 | 5 ± 2.7 | 13 ± 5.1 | 1 ± 0 | 1 ± 0 |
| 8 | 40 ± 3 | 0 | 4 ± 0 | 38 ± 6 | 24 ± 2.7 | 10 ± 3 | 34 ± 7.4 | 0 | 0 |
| 10 | 0 | 0 | 0 | 28 ± 8.3 | 10 ± 2.9 | 5 ± 1.3 | 8 ± 2.3 | 2 ± 2.3 | 0 |
| 12.5 | 0 | 6 ± 2.3 | 0 | 8 ± 2.3 | 0 | 0 | 0 | 0 | 0 |
| 14 | 0 | 0 | 0 | 22 ± 6.4 | 6 ± 1.3 | 2.5 ± 1.2 | 3 ± 1.3 | 0 | 0 |
| 16 | 6 ± 2.2 | 0 | 0 | 24 ± 7.6 | 4 ± 1.7 | 2 ± 1.3 | 9 ± 3.6 | 0 | 0 |
| 18 | 0 | 0 | 0 | 24 ± 6.3 | 4 ± 1.3 | 0 | 0 | 0 | 0 |
| 20 | 0 | 0 | 0 | 5 ± 0 | 4 ± 0 | 3 ± 0 | 1 ± 0 | 0 | 0 |
| 22 | 2 ± 1.3 | 0 | 0 | 4 ± 1.3 | 10 ± 3 | 0 | 0 | 0 | 0 |
| 10–22* | 8 ± 3.5 | 6 ± 2.3 | 0 | 115 ± 32.2 | 40 ± 11.2 | 12.5 ± 3.8 | 21 ± 7.2 | 2 ± 7 | 0 |

Replicate samples at each medium perfusion rate and inoculum density were pooled and are each tabulated as one mean ± SEM. Cumulative CFU-GM production after week 8 is statistically greater in the 3.5/wk cultures than the corresponding cultures perfused at 7/wk or 1/wk at all inoculum densities at the 1% level of significance.

schedule and inoculum density (Table 2). The medium perfusion rate had a pronounced effect on the number of granulocyte-macrophage progenitor cells produced. The 3.5/wk medium exchange cultures showed the greatest longevity in terms of progenitor cell production. These cultures produced progenitors at a stable rate between weeks 4 and 18.

The optimum conditions in terms of progenitor cell production are the cultures exchanged 3.5 times per week and inoculated at $5 \cdot 10^6$ cells/ml. These cultures produced a significant number of progenitor cells until week 20. Statistical analysis, using a paired t-test, showed that the optimum medium exchange rate cultures of 3.5/wk produced significantly more granulocyte-macrophage progenitor cells after week 8 than did the corresponding 7/wk and 1/wk cultures at all three inoculation densities at the 1% level of significance. The number of progenitor cells produced is important This result supports the hypothesis that long-term human Dexter culture conditions are suboptimal and as a culture in vitro better approximate the hematopoietic environment in vivo, more effective reconstitution of bone marrow ex vivo can be attained.

Physical appearance: The medium exchange rate significantly affected the physical appearance of the cultures. By 10 weeks in culture, the 7/wk cultures had large number of adipose cells in the stroma while the 3.5/wk cultures had few fat cells and the 1/wk cultures never developed fat cells. At culture termination at 26 weeks, the stroma of the 7/wk cultures were composed of approximately 20–30% fat cells while the 3.5/wk cultures still only had a few fat cells. Adherent colony distribution also varied between cultures with different medium perfusion rate. Adherent colonies in the 3.5/wk cultures persisted longer than those in the 7/wk and 1/wk cultures.

TABLE 3

Nonadherent cell morphology as a function of the medium perfusion rate and inoculum density.

| Medium perfusion rate | weeks | 5 × 10⁶ per ml | | | 2 × 10⁶ per ml | | | 1 × 10⁶ per ml | | |
|---|---|---|---|---|---|---|---|---|---|---|
| | | % Mφ | % G | % myeloid precursors | % Mφ | % G | % myeloid precursors | % Mφ | % G | % myeloid precursors |
| 7/wk | 10.4 | 25 | 57 | 18 | 57 | 32 | 11 | 52 | 34 | 14 |
| | 13.4 | 49 | 34 | 17 | 92 | 5 | 3 | 63 | 22 | 15 |
| | 15.4 | 66 | 19 | 16 | 79 | 19 | 2 | 54 | 17 | 29 |
| | 19 | 93 | 5 | 1 | 96 | 3 | 1 | 100 | 0 | 0 |
| 3.5/wk | 10.4 | 50 | 27 | 23 | 45 | 38 | 17 | 39 | 45 | 17 |
| | 13.4 | 23 | 59 | 19 | 27 | 56 | 17 | 36 | 47 | 17 |
| | 15.4 | 41 | 38 | 21 | 44 | 27 | 29 | 67 | 13 | 21 |
| | 19 | 58 | 37 | 5 | 88 | 9 | 3 | 99 | 1 | 0 |
| 1/wk | 10.4 | 59 | 21 | 20 | 60 | 11 | 29 | ND | ND | ND |
| | 13.4 | 56 | 25 | 20 | 19 | 36 | 46 | 43 | 7 | 50 |
| | 15.4 | 76 | 4 | 20 | ND | ND | ND | 46 | 39 | 15 |
| | 19 | 100 | 0 | 0 | 100 | 0 | 0 | 100 | 0 | 0 |

Data are for pooled replicate samples at each medium perfusion rate and inoculum density and are shown as the percentage of macrophages (% Mφ), granulocytes (mature granulocytes and bands, % G), and immature granulocytes (metamyelocytes and less mature cells, % myeloid precursors).

II. Medium Replacement Combined with Supplementation of Medium with Hematopoietic Growth Factors

Materials and Methods

Cells: Human bone marrow cells were obtained following informed consent from heparinized aspirates of the iliac crest bone marrow, under a protocol approved by the University of Michigan Human Investigation Committee. The bone marrow was separated by a Ficoll-Paque (Pharmacia) density gradient centrifugation and the low density cells (<1.077gm/cm³) were collected and washed 3 times with IMDM. The cells were counted between the second and third washes. The cells were then seeded onto 6-well tissue culture plates (Costar No. 3406) or collagen coated 6-well plates (rat tail type 1 collagen, Biocoat. Collaborative Research Inc. Cat. No. 40400) in duplicate 5·10⁶ cells/ml at 1.5 ml/well.

Culture medium: The medium used was IMDM (Gibco Laboratories. Cat. No. 430-2200) containing 10% fetal calf serum (Hyclone Laboratories), 10% horse serum (Hyclone Laboratories), 1% penicillin/-streptomycin (Sigma, 10,000 U/ml penicillin G and 10 mg/ml streptomycin, Cat. No. P3539), and $10^{-5}$M hydrocortisone (17-Hydroxycorticosterone, Sigma, Cat. No. H0888).

Hematopoietic growth factors (HGH): Due to the frequent culture supplementation via rapid medium exchange, hematopoietic growth factors were added to the medium at approximately 1/20 of the concentrations found to promote maximal colony formation in clonal assays 4. The concentrations used were 1 ng/ml of IL-3, 1 ng/ml of GM-CSF (Amgen Biologicals, Cat. No. 13050), 0.1 U/ml of Epo (Terry Fox Labs. Vancouver, Canada).

Hematopoietic progenitor cell assay: Nonadherent hematopoietic cells removed from culture were counted and plated at 1·10⁵ cells/ml or fewer cells in methylcellulose. GM-CSF and Epo were added to the methylcellulose at 20 ng/ml and 2 U/ml, respectively. The cell were plated in 24 well plates at 0.25 ml/well and incubated at 37° C. for 14 days. The colonies were then counted under an inverted microscope and colonies greater than 50 cells were scored as GM-colony forming units (CFU-GM), erythroid burst-forming unit (BFU-E), or granulocyte erythroid megakaryocyte macrophage-colony forming unit (CFU-GEMM).

LTBMC conditions: The cultures were incubated at 37° C. in a humidified 5% $CO_2$/95% air atmosphere and perfused (medium exchanged) at a rate of 50% daily medium exchange. During the first week in culture, all cells removed during the daily medium exchange were centrifuged and returned to the original wells. After the first week in culture, 50% of the total nonadherent cells were removed from the cultures on a biweekly basis during the medium exchange, mononucleated cells counted, and fresh medium returned to the wells. The remaining five days per week when the cells were not counted, 50% of the medium was removed from each of the culture wells and replaced with fresh medium, the removed medium was centrifuged, the medium decanted from the cell pellet, and the cells returned to their original wells.

Statistical analysis: The probability of significant differences between groups of cultures was determined by comparing the normalized cumulative cell production values from the rapidly perfused cultures supplemented with hematopoietic growth factors to the matched untreated control cultures using a paired t-test. Statistical significance was taken at the 5% level. There were no statistical differences between matched rapidly perfused LTBMCs cultured on tissue culture plastic and type I rat tail collagen at the 5% level. Therefore, the data for the plastic and collagen matrix were combined for presentation in this and all other figures and statistical analysis performed on the combined data.

Results

Kinetics of cell production in rapidly exchanged growth factor supplemented LTBMCs: As a first test of the hypothesis that the longevity and productivity of long term bone marrow cultures (LTBMCs) is limited by insufficient production of HGF's, we maintained rapidly exchanged ex vivo bone marrow cultures that were supplemented with IL-3, or Epo. In these cultures, 50% of the medium was removed daily and replaced with an equal volume of fresh medium supplemented with IL-3 or Epo. The cells removed were then centrifuged, the medium decanted and discarded, the cells resuspended, and the cells returned to the original cultures. IL-3 and Epo individually enhanced the cell productivity of rapidly exchanged LTBMCs. The cultures containing Epo alone initially had a high cell production rate due to substantial terminal erythroid differentiation. However, by week four erythropoiesis had ceased and the cell production rate had decreased to the level of the control cultures. IL-3 and Epo induced an average increase in nonadherent cell production over controls throughout the 18 weeks of culture of 175% and 173%, respectively.

Combinations of growth factors proved to be more effective in increasing the nonadherent cell production rate. The highest rate of cell production was observed for the combination of IL-3+GM-CSF+Epo. These cultures produced approximately 25% of the number of cells inoculated biweekly during the first 6 weeks in culture and had an average 4.8-fold increase in nonadherent cell production over controls during weeks 2–8. The combination of IL-3+GM-CSF produced an average 3.5-fold increase in nonadherent cells as compared to controls through week 8. In separate experiments, adding neither IL-6 nor G-CSF to the combination of IL-3+GM-CSF+Epo improved the nonadherent cell production rate, but instead resulted in cell production rates indistinguishable from the cultures containing the combination of IL-3+GM-CSF. In all cases, the stimulatory effect on cell production induced by the addition of HGFs was maximal between weeks 0 to 8, although cell production was higher than the controls throughout the culture.

The combinations of HGFs lead to high absolute numbers of nonadherent cells produced in rapidly exchanged LTBMCS. The productivity of the cultures can be shown by comparing the cumulative number of cells produced over time ($\Sigma_{i=1}^{n}$, $C_i$, $C_i$ being the number of nonadherent cells collected at time i), relative to the number of cells inoculated ($C_o$) by plotting the ratio ($\Sigma_{i=1}^{n}$, $C_i$, $C_o$) as a function of time. When this ratio exceeds unity, a culture has produced more cells than were inoculated and the culture has led to an expansion in cell number.

The combination of IL-3+GM-CSF+Epo induced cumulative cell production that was more than 3-fold greater than the number of cells inoculated. The cell production rate was the highest during the first 6 weeks in culture during which time the culture produced approximately as many cells as were inoculated every two weeks. This maximum cell production rate was 15% of the estimated in vivo bone marrow cell production rate where 50% of the myeloid cell mass is generated daily. The combination of IL-3+GM-CSF resulted in more than a 2-fold expansion in cell number and at rates comparable to the combination of IL3+GM-CSF+Epo during weeks 3–7 in culture. Untreated rapidly exchanged (50% daily medium exchange) and slowly exchanged (50% medium exchange biweekly) control cultures not supplemented with HGFs produced approximately 1 and 0.37 times the number of cells inoculated after 18 weeks, respectively. More importantly more than half of all cells removed from these unsupplemented cultures came from the first two samplings, indicating that many of these cells were from the original inoculum and that supplementation of the cultures with HGFs are required to induce significant cycling of progenitor and stem cells.

Morphologic analysis of nonadherent cells: The addition of multiple HGFs also increased the variety of myeloid cells produced in the cultures. The control cultures produced nonadherent cells that were predominately macrophages after week 3 in the culture. Production of erythroid cells decreased rapidly with few erythroid cells detected after week 5. The cultures containing Epo (Epo alone, IL-3+Epo, and IL-3+GM-CSF+Epo) produced a transient increase in erythroid cell production, with a high percentage (55–75%) of nonadherent cells being erythroid through week 3. When IL-3+Epo±GM-CSF was present, the cultures continued to produce erythroid cells throughout the 16 weeks in culture with about 5–15% of the nonadherent cells being typed as erythroid. Thus, in the presence of IL-3+Epo, erythropoiesis was active throughout.

IL-3±Epo led to a nonadherent cell population that was predominately (60–70%) late granulocytes (LG) at week 5. The percentage of LGs steadily declined until it reached about 20% at week 18. The production of macrophages rose correspondingly. When GM-CSF was added to IL-3±Epo, the high percentage of LG persisted through 18 weeks. The combination of IL-3+GM-CSF thus led to active granulopoiesis for 18 weeks in culture, and the addition of Epo maintained erythropoiesis as well. Photomicrographs of the control and IL-3+GM-CSF+Epo supplemented cultures at 5.5 weeks in culture show the dramatic enhancement in culture density and variety of cells produced.

Kinetics of nonadherent progenitor cell production: Progenitor cell production increased with the addition of multiple HGFs. The production of granulocyte macrophage colony forming units (CFU-GMs) in the untreated controls was prolonged and steady for over 18 weeks, which is consistent with the earlier results obtained using rapidly perfused LTBMC without HGF. CFU-GM produced in the IL-3+GM-CSF and IL-3+Epo±GM-CSF cultures was approximately 10-fold higher than controls during weeks 3 to 5.

Erythroid burst forming unit (BFU-E) production in human LTBMC has been reported to be low and cease quickly (Coutinho et al, *Blood* (1990) 75(11): 2118–2129). The rapidly exchanged, untreated controls exhibited a rapid decrease in BFU-E production although low levels of BFU-E were produced through 17 weeks in culture. The addition of Epo alone did not significantly influence the number of BFU-Es produced. IL-3 alone induced a mild short-lived stimulation of BFU-E production in weeks 3–5. On the other hand, IL-3 plus either Epo or GM-CSF induced a 10 to 20-fold elevation of nonadherent BFU-E levels compared to that of controls during weeks 3 to 5 of culture.

III. Transformation of human stem cells

Materials and Methods

Cells Human bone marrow cells were obtained following informed consent from heparinized aspirates of the iliac crest bone marrow, under a protocol approved by the University of Michigan Human Investigation Committee. The bone marrow was separated by a Ficoll-Paque (Pharmacia) density gradient centrifugation and the low density cells ($<1.077$ gm/rm$^3$) were collected and washed 3 times with IMDM. The cells were counted between the second and third washes. For the CD18 gene transfer experiments, bone marrow was obtained following informed consent from a CD18 deficient patient donor.

Lineage negative (Lin$^-$) selection of bone marrow cells Mature mononuclear cells were removed from the above cell preparation by incubating the cells with a mixture of monoclonal antibodies (MAb) after the third wash with IMDM. $10^7$ cells were incubated in 1 ml of MAb cocktail on ice for 1 hour with gentle mixing every 10–15 minutes. The MAb cocktail used is shown in Table 4.

TABLE 4

Preparation of monoclonal antibodies used to separate lineage+ bone marrow mononuclear cells.

| Monoclonal Antibody | Specificity | Cat. No. | Conc. µg/10⁹ cells | Volume (µl) |
|---|---|---|---|---|
| Anti-Leu-1 | T-cell | 6300 | 30 | 125 |
| Anti-Leu-5b | T-cell, E-rosette receptor | 7590 | 32 | 16 |
| Anti-Leu-10 (Anti-HLA-DQ) | B-cells, monocytes | 7450 | 250 | 125 |
| Anti-Leu-12 | B-cells | 7540 | 120 | 60 |
| Anti-CALLA | Common Acute Lymphoblastic Leukemia | 7500 | 60 | 60 |
| Anti-Leu-M1 | Monocytes, granulocytes | 7420 | 1000 | 500 |
| Anti-MO-1 | Macrophages | — | 1000 µl | 1000 |
| Anti-10F-7 | RBCs | — | 2000 µl | 2000 |
| Anti-E3 | RBCs | — | 2000 µl | 2000 |

Add IMDM to make MAb cocktail total volume of 100 ml, filter sterilize, aliquot in 1 ml columns, and store at −20° C.

The cells were washed 3 times in excess ice cold IMDM and centrifuged at 4° C. An appropriate amount of magnetic goat anti-mouse Ig (Biomag; Collaborative Research Corp., Cat. No. 74340-50, 1 mg/ml, $5 \times 10^8$ particles/ml) was washed 3 times in ice cold IMDM and centrifuged. The cells were resuspended in Biomeg at 50 particles/cell and placed in a T-25 or T-75 tissue culture flask and incubated on ice for ½ hour with intermittent shaking. After incubation, the flask was laid onto flat magnet, the magnet secured to the flask and incubated at 4° C. for 10–15 minutes. The magnet and flask were stood upright and the supernatant collected. The incubation with shading, adding magnet, standing upright, and collecting supernatant was repeated 2 more times. The cells were counted and seeded onto 6-well tissue culture plates. (Costar No. 3406).

Culture medium The medium used was IMDM (Gibco Laboratories, Cat. No. 430-2200) containing 10% fetal calf serum (Hyclone Laboratories), 10% horse serum (Hyclone Laboratories), 1% penicillin/streptomycin (Sigma, 10,000 U/ml penicillin G and 10 mg/ml streptomycin, Cat. No. P3539), and $10^{-5}$M hydrocortisone (17-Hydroxycorticosterone, Sigma, Cat. No. H0888).

Hematopoietic growth factors The hematopoietic growth factors were the optimum discussed above. The concentrations used were 1 ng/ml or 0.4 U/ml of IL-3 (a gift from Genetics Institute, Cambridge, Mass.), 1 ng/ml of GM-CSF (a gift from Genetics Institute, Cambridge, Mass.), 50 U/ml of IL-1a (Genzyme Corp.), 0.1 U/ml of Epo (Terry Fox Labs, Vancouver Canada), 10 ng/ml MGF (mast cell growth factor, the c-kit ligand, Immunex Corp., Seattle, Wash.), and 2.0 ng/ml Hybrikine ([PIXY321] Immunex Corp., Seattle, Wash.).

Hematopoietic progenitor cell assay Nonadherent hematopoietic cells removed from culture during the weekly sampling were counted and plated at $1-10^5$ cells/ml or fewer cells in methylcellulose. MGF, GM-CSF and Epo were added to the methylcellulose at 50 ng/ml, 20 ng/ml, and 2 U/ml, respectively. The cells were plated in 24 well plates at 0.25 ml/well and incubated at 37° C. for 14 days. The colonies were then counted under an inverted microscope and colonies greater than 50 cells were scored as a GM-colony forming units (CFU-GM), erythroid burst-forming unit (BFU-E), or granulocyte erythroid megakaryocyte macrophage-colony forming unit (CFU-GEMM).

Retroviral producer cell lines Two retroviral producer cell lines were obtained from Dr. Eli Gilboa's Laboratory at Memorial Sloan Kettering Cancer Center, New York, N.Y. The cell line produce amphotrophic viral particles that contain the NEO gene which produces neomycin phosphotransferase providing resistance to the mammalian neomycin analog G418. Also both cell lines produce retroviral particles that are deficient in the required retroviral genes so that cells infected with the retrovirus cannot themselves produce infectious virus.

The SAX containing packaging cell line is a 3T3 based cell line which contains a modified Moloney Murine Leukemia Virus (MoMuLV). The SAX provirus contains the NEO gene, an SV40 promoted Adenosine deaminase gene, in a XhoI restriction site. Also, the SAX provirus contains the Ψ packaging region but is deficient in the gag (core proteins), pol (reverse transcriptase), and env (envelope proteins) genes. This second retroviral particle contains a double copy of the foreign DNA and the retroviral particles are denoted DC-29 (double copy-29th clone). The DC-29 provirus contains two copies of the NEO gene and other retroviral and foreign DNA in a 3T3 cell line.

For the CD18 experiments, the amphotropic packaging cell Psi-Crip infected with a retroviral vector containing a human full length CD19 cDNA was used (Wilson et al, Science (1990) 248:1413–1416). In this retrovirus, a full length cDNA for human CD18 was cloned into the BamH1 site of a vector that expresses the recombinant gene from heterologous sequences spanning the 5' region of the chicken β-actin gene called BA-CD18. Sequences 5' to the immediate early (IE) gene of human cytomegalovirus were subcloned into PUC19 and a portion containing IE enhancer sequences was removed on a Xho 1(from the polylinker) to Nco 1(−220 of the IE gene) fragment). Synthetic linkers were used to convert the NcoI site to a XhoI site and the modified fragment was cloned into the unique XhoI site of BA-CD18 located 5' to the β-actin promoter. This new vector was called CMV-BA-CD18.

Retroviral particle production The SAX retroviral particles were provided by Dr. Clay Smith in Dr. Eli Gilboa's laboratory as viral supernatant solutions frozen and stored at −80° C. The DC-29 and CD18 retroviral particles were produced by growing the DC-29 and CD18 viral packaging line to near confluency in a T-75 flask, changing all the medium, incubating the cells for 12–15 hours and then collecting the medium containing the viral particles. The virus containing supernatant was then centrifuged to remove vital packaging cells, the medium removed, and frozen in aliquots at −80° C.

LTBMC with supernatant added SAX retrovirus. DC29 retrovirus, or CD18 retrovirus The cultures were incubated at 37° C. in a humidified 5% $CO_2$/95% air atmosphere. During the two first weeks in culture, two thirds of the medium (1 ml) was removed from each culture well daily and the medium replaced with an equivalent volume fresh medium containing HGF's (0.85 ml) and viral cell producer supernatant; (0.15 ml). The retroviral supernatant containing medium was thawed immediately prior to use and if not completely urged, it was stored on ice in a refrigerator. The medium removed from the cultures was centrifuged, the medium decanted, and the cells returned to the original wells.

LTBMC co-cultured with SAX retrovirus packaging cell line The SAX retrovirus packaging cell line was grown to approximately 10% confluency in T-25 flasks (Costar, No. 3056) and then subjected to 2000 rads of radiation. The hematopoietic cells prepared above were added to the irradiated viral producer cells and cultured wit 50% daily medium exchange for 2.5 weeks with all cells being returned to the wells. At 2.5 weeks in culture, a 0.5 mM solution of EDTA was added to the flasks to remove the hematopoietic cells while leaving the stroma. The removed hematopoietic cells were added to 3 wells of a 6 well plate with 1000 freshly trypsinized bone marrow fibroblast cells per well.

Sampling of infected LTBMCs Beginning at week two in culture, after retrovirus addition had ended or co-culture had ceased, the cultures had 50% medium exchanged per day with the nonadherent cells in the exchanged medium being removed once per week for analysis. Nonadherent cells were removed from the cultures during the daily medium exchange, the mononucleated cells counted, and fresh medium returned to the wells. The remaining six days per week when the cells were not counted, 50% of the medium was removed from each of the culture well sand replaced with fresh medium, the removed was centrifuged, the medium decanted from the cell pellet, and the cells returned to their original wells.

Analysis for retroviral infection The initial bone marrow inoculum was plated in 0, 0.4, 0.8, 1.2, 1.6, and 2.0 mg/ml G418 to obtain a kill curve to determine the concentration of G418 in which to plate the post-infected bone cells. Cells removed from the cultures were plated in methylcellulose with G418 at 0.0, 0.8, and 1.6 mg/ml G418. After two weeks, the number of progenitor cell colonies were enumerated in the methylcellulose. Individual colonies were then plucked from the methylcellulose and assayed by polymerase chain reaction (PCR) for retroviral DNA.

Statistical analysis The probability of significant difference between groups of cultures was determined by comparing the cumulative cell production values from the experimental samples to the matched control cultures using a paired t-test. Statistical significant was taken at the 5% level.

Results
Retroviral infection using SAX retrovirus

Kinetics of cell production in LTBMCs infected with SAX retrovirus Cell production in retrovirally-infected cultures is an indicator of the likelihood of retroviral infection and is therefore a useful parameter to measure. Retroviral integration into the target cell genome is only thought to occur during cell division. For this reason, increased culture productivity increases the probability of stem cell mitosis and thereby increases the probability of retroviral infection. The highest cell production occurred in the cultures with supernatant virus addition supplemented with IL-3+GM-CSF and IL-3+GM-CSF+IL-1α which produced increasing number of cells through 4 weeks in culture. The LTBMCs co-cultured with the SAX virus packaging cells produced more cells than the supernatant addition cultures at week two, although cell production decreased after week 2.

Analysis of retroviral infection in LTBMCs with supernatant SAX virus addition The percentage of progenitor cells surviving in high G418 concentration varied from 2 to 50% in the cultures supplemented with IL-3+GM-CSF or IL-3+GM-CSF+IL-1α during the first four to six weeks in culture. By 10 weeks in culture (8 weeks after virus addition had ended) 43% of the number of progenitor cells that were clonable to hematopoietic colonies survived exposure to G418. This indicates that these progenitor cells had been rendered G418 resistant by virtue of containing the G418 resistance gene transferred by the retrovirus to stem cells present in the culture during the initial 14 day infection period. The rapidly perfused cultures not supplemented with HGFs had an average 12% progenitor cell survival in high G418 concentration between weeks 8 and 11. At culture termination at 11 weeks, the stromal layer of the IL-3+GM-CSF supplemented cultures was trypsinized and 17% of progenitor cells that were adherent to the stroma survived in high G418 concentration. This suggests that a significant percentage of adherent progenitor cells were also infected with the SAX virus.

Analysis of retroviral infection in LTBMCs co-cultured with irradiated SAX virus packaging cells The percentage of progenitor cells surviving in G418 when co-cultured with irradiated SAX cells varied between 0 and 36%. The cultures not supplemented with HGFs produced CFU-GM that survived in high [G418] only between weeks 4–7. After week 7, no CFU-GM were produced in these cultures that survived in high G418 concentration, suggesting that little or no infection of stem cells occurred. The LTBMCs supplemented with IL-3+GM-CSF and co-cultured with irradiated SAX cells for 2.5 weeks produced high percentages of CFU-GM that survived in 0.8 mg/ml G418 at weeks 4, 5 and 8. However, at week 10, these cultures failed to produce CFU-GM that were resistant to G418. This suggests that little or no infection of stem cells occurred in these cultures or that the stem cells may have differentiated or died.

Retroviral infection using DC-29 retrovirus

Kinetics of cell production in LTBMCs infected with DC-29 retrovirus The number of cells produced in the cultures infected with DC-29 retroviral supernatant was HGF dependent. The cultures supplemented with IL-3+GM-CSF+Epo produced between $1.5-4 \times 10^6$ cells on a weekly basis throughout the 10 weeks of culture. The cultures supplemented with IL-3+GMCSF+Epo+MGF were more prolific, while the cultures supplemented with Hybrikine+Epo resulted in the highest cell production. Interestingly, the control cultures supplemented with IL-3+GM-CSF+Epo but not receiving DC-29 retroviral supernatant additions were less prolific than the similar cultures receiving the DC-29 retroviral supernatant. Cell production in the IL-3+GM-CSF+Epo, IL-3+GM-CSF+Epo+MGF and Hybrikine+Epo cultures (with virus addition) was significantly higher than the control culture (IL-3+GM-CSF+Epo, no virus addition) at the 5%, 1% and 1% level of significance, respectively. A part of the increased production in the cultures with retroviral supernatant addition may be due to the presence of a growth factor(s) such as MGF (c-kit ligand) which is known to be produced by the 3T3-based packaging cell line.

Analysis of retroviral infection in LTBMCs with supernatant DC-29 virus addition The efficiency of retroviral infection was assessed by CFU-GM survival in 1.6 mg/ml G418, a concentration that killed all bone marrow cells prior to retroviral infection. The average percent of CFU-GM surviving at week 8 (6 weeks after infection) was high in all infected cultures, Table 5.

TABLE 5

Percent of CFU-GM surviving in 1.6 mg/ml G418 after infection with DC-29 retrovirus as a function of HGF supplementation. The cultures were infected with DC-29 retroviral containing supernatent for the initial 2 weeks in culture.

| | IL-3 + GM-CSF + Epo with virus | | | | | IL-3 + GM-CSF + Epo + MGF with virus | | | | | Hybrikine + Epo with virus | | | | |
|---|---|---|---|---|---|---|---|---|---|---|---|---|---|---|---|
| week | 1 | 2 | 3 | ±dev. | ave. | 1 | 2 | 3 | ±dev. | ave. | 1 | 2 | 3 | ±dev. | ave. |
| 2 | 4.70 | 2.40 | 5.60 | 1.6 | 4.2 | 3.70 | 21.6 | 19.5 | 9.7 | 1.49 | 9.00 | 6.20 | 18.4 | 6.4 | 11.2 |
| 4 | 2.5 | 0.0 | 4.6 | 2.5 | 2.4 | 8.1 | 6.0 | 16.1 | 3.3 | 10.1 | 9.0 | 6.2 | 18.4 | 5.4 | 4.4 |
| 6 | 0.0 | 0.0 | 0.0 | 0.0 | 0.0 | 1.4 | 1.7 | 4.0 | 1.4 | 2.4 | 0.0 | 0.0 | 0.0 | 0.0 | 0.0 |
| 8 | 0.0 | 22.2 | * | 12.8 | 7.4 | 0.0 | 14.5 | 11.5 | 3.6 | 9.0 | 21.6 | 14.7 | 10.7 | 5.5 | 15.7 |
| 10 | * | 0.0 | * | 0.0 | 0.0 | 8.2 | 0.0 | 0.0 | 4.7 | 2.7 | 0.0 | 0.0 | 0.0 | 0.0 | 0.0 |
| 10 | 2.6 | 0.0 | * | 1.5 | 0.9 | 7.7 | 0.0 | * | 4.4 | 2.6 | 0.0 | 0.0 | 0.0 | 0.0 | 0.0 |

*N/A because no CFU-GM were counted in 0.0 mg/ml G418,
% CFU-GM surviving in 1.6 mg/ml G418 from the trypsinized stroma in each culture at experiment termination
% survival was calculated as the (number of CFU-GM at 1.6 mg/ml G418 - ave. number of CFU-GM at 1.6 mg/ml G418 in uninfected cultures) divided by (number of CFU-GM at 0.0 mg/ml G418) * 100

Addition of MGF to the combination of IL-3+GM-CSF+Epo appears to have increased infection efficiency at weeks 8–10 in culture, with one of the cultures containing 7.7% G418 resistant colonies. The data at week 8 suggests that the cultures supplemented with Hybrikine+Epo had a high infection efficiency, although the data at week 10 suggests no infection. At week 10, note that the number of CFU-GM removed from several cultures decreased to where few or no CFU-GM would be expected be seen at approximately 10% infection. In addition, 1.5 mg/ml G418 is an extremely high antibiotic dose, enough to likely overwhelm the efficacy of the G418 resistance gene transfected at even slightly suboptimal levels. Thus, the efficiency of gene transfer into the hematopoietic stem cells in these cultures was at least 7.7% in some samples, and perhaps as high as 45% or higher.

Kinetics of nonadherent progenitor cell production

Because analysis of retroviral infection in these experiments depends on assaying for progenitor cells to infer stem cell existence, infection, and cycling, it is important to determine the effect of HGFs on progenitor cell production in culture. Also, in this retroviral experiment, MGF and Hybrikine are being used in combination with other HGFs. Both MGF and Hybrikine have not been used in rapidly perfused HGF supplemented LTBMCs, and it is therefore necessary to determine their effects on hematopoiesis.

Progenitor cell production was strongly dependent on HGF supplementation. The number of CFU-GM removed from the cultures is shown in Table 6.

TABLE 6

The cumulative number of progenitor cells removed in DC-29, HGF supplemented rapidly perfused human long-term bone marrow cultures.

| Culture | Virus Added | Total Number of CFU-GM Removed |
|---|---|---|
| Innoculum | N/A | 900 |
| Control (IL-3 + GM-CSF + Epo) | No | 1300 |
| IL-3 + GM-CSF + Epo | Yes | 2800 |
| IL-3 + GM-CSF + Epo + MGF | Yes | 5400 |
| Hybrikine + Epo | Yes | 5000 |

Every second weekly sampling from the cultures was assayed for CFU-GM and the non assayed values were estimated by linear interpolation between two known data points. The known and interpolated values were summed to approximate the total number of CFU-GM removed from culture.

Addition of retroviral supernatant increased progenitor cell removal 2.2-fold over no addition of retroviral supernatant. The increase in the number of CFU-GM removed in the cultures supplemented with retroviral supernatant and IL-3+GM-CSF+Epo+MGF or Hybrikine+Epo was 4.2 and 3.8-fold greater then the uninfected control, respectively. Removal of CFU-GM was statistically greater, at the 1% level of significance, in all viral supplemented cultures when compared to the number of CFU-GM inoculated.

Progenitor cells production in culture

A population balance on the CFU-GM compartment shows that the addition of MGF or Hybrikine to cultures supplemented with IL-3+GM-CSF+Epo have a significant positive effect on the CFU-GM pool. The addition of MGF to the combination of IL-3+GM-CSF+Epo increased CFU-GM removal 1.9-fold and CFU-GM differentiation 0.5-fold compared to similar cultures not supplemented with MGF, Table 7.

TABLE 7

The cumulative production of CFU-GM removed and differentiated in growth factor supplemented DC-29 retroviral infected rapidly perfused human long-term bone marrow cultures.

| Culture | Number of CFU-GM removed (plated) | Number of GM cells removed ($\times 10^{-6}$) | Estimated number of CFU-GM that differentiated | Total number of CFU-GM |
|---|---|---|---|---|
| Innoculum | (900) | (0) | (0) | (900) |
| control (IL-3 + GM-CSF + Epo, no virus added) | 1300 | 1.1 | 1100 | 2400 |
| IL-3 + GM-CSF + Epo (virus added) | 2800 | 1.8 | 1800 | 4600 |
| IL-3 + GM-CSF + Epo + MGF (virus added) | 5400 | 3.1 | 3100 | 8400 |
| Hybrikine + Epo | 5000 | 6.1 | 6100 | 11,100 |

TABLE 7-continued

The cumulative production of CFU-GM removed and differentiated in growth factor supplemented DC-29 retroviral infected rapidly perfused human long-term bone marrow cultures.

| Culture | Number of CFU-GM removed (plated) | Number of GM cells removed ($\times 10^{-6}$) | Estimated number of CFU-GM that differentiated | Total number of CFU-GM |
|---|---|---|---|---|
| (virus added) | | | | |

Every second weekly sampling from the cultures was assayed for CFU-GM and the non assayed values were estimated by linear interpolation between two known data points. The known and interpolated values were summed to approximate the total number of CFU-GM removed from culture.

The combination of Hybrikine+Epo had a very pronounced effect on CFU-GM production and differentiation. Hybrikine+Epo induced a 1.8-fold increase in CFU-GM removal and over a 3-fold increase in CFU-GM differentiation compared to the previous optimum cultures supplemented with IL-3+GM-CSF+Epo. Also, Hybrikine+Epo induced production of almost twice the number of granulocytes and macrophages than did the combination of IL-3+GM-CSF+Epo+MGF. This indicates that Hybrikine is a potent inducer of the granulocyte macrophage lineages.

Analysis of neutrophils produced from stem cells infected with CD18 encoding retrovirus CD18 deficient bone marrow was enriched for early hematopoietic cells as described above, and then cultured for 14 days with 50% daily medium exchange supplemented with 1.0 ng/ml/day GM-CSF and 1.0 ng/ml/day IL-3 and 40 U/ml/day IL-1α, and with CD18 retroviral producer line supernatant. From day 15 on, the cells were cultured under the same conditions without addition of retroviral supernatant. Nonadherent cells were removed from the cultures weekly and analyzed for the presence of cell surface CD18 by flow cytometry using a biotinylated anti-CD18 monoclonal antibody by standard methods (Updyke et al *Meth. Enzymol.* (1986) 121:717–725). Whereas CD18 deficient bone marrow cells failed to express any cell surface CD18 protein by this assay, neutrophils and monocytes that arose from the retrovirally infected cultures did express cell surface CD18. In triplicate cultures, expression of cell surface CD18 was 3.5%/5%/2% at 6 weeks and 11%/28%/3% at 11 weeks. Since the neutrophils and monocytes present in the cultures at 11 weeks arose form CFU-GM progenitor cells only 10–14 days earlier, these data indicate that human hematopoietic stem cells were successfully and stably transfected with the recombinant retrovirus during the first two weeks of the culture.

In interpreting the present results it is important to recognize that although several groups have demonstrated retroviral-mediated gene transfer into human hematopoietic progenitor cells, gene transfer into human hematopoietic stem cells has not been shown. The rapid decay of cell production in traditional, slowly perfused human LTBMCs limited infection determination due to the absence of progenitor cells required for the assay.

Retroviral infection in the present studies was initially assessed by growing cells removed from the LTBMCs in methylcellulose in the presence of the mammalian cell antibiotic G418. Progenitor cells infected with the SAX or DC-29 retroviruses and expressing the NEO product will be able to survive and form colonies in high concentrations of G418, whereas noninfected cells will die in high concentrations of G418. Also, production of progenitor cells that survive in high concentrations of G418, six or more weeks after virus addition has ended, requires those cells to have recently differentiated from a more primitive cell (a stem cell) and therefore suggests that stem cells were infected. Similarly, the CD18 expressed on the surface of neutrophils and monocytes produced during the 11th week of culture requires that a primitive hematopoietic stem cell was infected during the first 2 weeks of the cultures, because all mature cells, precursors, and clonogenic progenitors present during the infection period had died by 4–5 weeks in the culture.

The analysis for retroviral infection used here can underestimate the percentage of cells infected with the retrovirus due to insufficient expression of the NEO gene product. Under-expression of the transferred gene product has been shown to be a problem in human and primate models. Therefore, the percentage of progenitor cells infected in this study is probably a conservative estimate.

The percentage of progenitor cells that survived in high G418 concentration was approximately 40% at week 10 in the cultures infected SAX retrovirus supernatant and supplemented with IL-3+GM-CSF±IL-1α. These initial results show that a high percentage of stem cells were infected in the cultures supplemented with retroviral supernatant during the first two weeks in culture.

The percentage of progenitor cells infected with the DC-29 retrovirus was high (0–21%) in the IL-3+GM-CSF+Epo+MGF and Hybrikine+Epo cultures during the initial 4 weeks after viral addition had ended. This high level of progenitor cell infection was probably due to direct infection of progenitor and primitive cells by the retrovirus. The percentage of progenitor cells surviving in high G418 concentration decreased 4 weeks after viral addition had ended, but rebounded 2 weeks later to 0–22% survival in high G418 concentration.

The production of G418 resistant progenitor cells in the DC-29 experiment may underestimate the percentage of progenitor cell actually infected with the DC-29 retrovirus. The high concentration of G418 used to select for infected colonies (1.6 mg/ml of G418) is twice as high as that used for the SAX infection experiment and requires high expression levels of the NEO gene product, neomycin phosphotransferase, to survive.

Interestingly, in the LTBMCs supplemented with either the SAX or DC-29 retrovirus containing supernatant, the HGFs IL-3+GM-CSF±Epo, IL-1α, or MGF or the combination of Hybrikine+Epo, the percent of progenitor cells surviving in G418 increased 6–8 weeks after viral addition ended. Although the mechanism for the increase in the percentage of G418 surviving progenitor cells towards the latter stages of the culture are not known one possibility is that stem cells that were infected during the first two weeks in culture became more active as the culture progressed. This would effectively increase the percentage of cells surviving in G418. Another possibility is that expression of the NEO gene may have increased in progenitor cells produced late in culture due to differentiation from a stem cell which had a different and better expressible integration site than did progenitor cells transfected directly during the initial infection culture period. Therefore, the high level of progenitor cell survival late in culture although possibly due to several causes, does strongly suggest that stem cells were infected in these LTBMCs.

In sum, these data document that under the culture conditions disclosed in the present invention, hematopoietic stem cells were proliferating in the cultures, permitting the incorporation of retrovirally transferred genetic material into these cells. Progenitors were continuously and actively produced from these stem cells, and these many of these progenitors contained and expressed the transfected genes. These data indicate that genetically modified human hematopoietic stem cells were present and proliferating in these cultures.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for obtaining ex vivo human hematopoietic stem cell stable genetic transformation comprising the following steps:
    (a) obtaining a human cellular composition containing human hematopoietic stem cells;
    (b) culturing said cells in the presence of a liquid culture medium containing a retroviral vector containing a heterologous gene for two weeks, wherein two thirds of said culture medium is removed from each culture daily and said medium is replaced with an equivalent volume of fresh medium containing hematopoietic growth factors and said retroviral vector;
    (c) thereafter replacing said culture medium with culture medium free of said retroviral vector;
    (d) thereafter replacing said retroviral-vector-free culture medium, either periodically or continuously, at a rate of 50% to 100% daily replacement, while maintaining said culture under physiologically acceptable conditions; and,
    (e) obtaining a cellular composition containing stable, genetically transformed human hematopoietic stem cells.

2. The method of claim 1 wherein said retroviral-vector-free culture medium is replaced continuously.

3. The method of claim 2, wherein replacement of said retroviral-vector-free culture medium comprises perfusing fresh medium through at least part of the mass of said human hematopoietic stem cells.

4. The method of claim 1, wherein said retroviral-vector-free culture medium is replaced periodically.

5. The method of claim 4, wherein replacement of said retroviral-vector-free culture medium comprises perfusing fresh medium through at least part of the mass of said human hematopoietic stem cells.

6. The method of claim 1, wherein said human cellular composition containing human hematopoietic stem cells is at least one member selected from the group consisting of human peripheral blood mononuclear cells, human bone marrow cells, human fetal liver cells, and human cord blood cells.

7. The method of claim 6, wherein said human cellular composition containing human hematopoietic stem cells have been enriched for said human hematopoietic stem cells.

8. The method of claim 1 wherein said stable, genetically transformed human hematopoietic stem cells obtained in step (d) produce stable, genetically transformed human hematopoietic progenitor cells.

9. The method of claim 6, wherein said stable, genetically transformed human hematopoietic stem cells obtained in step (d) produce stable, genetically transformed human hematopoietic progenitor cells.

10. The method of claim 1, wherein IL-3 and GM-CSF are added continuously to said retroviral-vector-free culture medium, each at a rate of 0.1 to 100 ng $ml^{-1} day^{-1}$.

11. The method of claim 1, wherein IL-3 and GM-CSF are added continuously to said retroviral-vector-free culture medium, each at a rate of 0.5 to 10 ng $ml^{-1} day^{-1}$.

12. The method of claim 1, wherein IL-3 and GM-CSF are added continuously to said retroviral-vector-free culture medium, each at a rate of 1 to 2 ng $ml^{-1} day^{-1}$.

13. The method of claim 10, wherein steel factor is added to said medium at a rate of from 1 to 100 ng $ml^{-1} day^{-1}$, or IL-1α is added to said medium at a rate of from 10 to 100 U $ml^{-1}$ per 3 to 5 day period.

14. The method of claim 13, wherein steel factor is added to said medium.

15. The method of claim 13, wherein IL-1α is added to said medium.

16. The method of claim 13, wherein both steel factor and IL-α are added to said medium.

17. The method of claim 1, wherein said retroviral-vector-free culture medium comprises animal sera or plasma.

18. The method of claim 1, wherein said retroviral-vector-free culture medium comprises a corticosteroid.

19. The method of claim 1, comprising maintaining glucose concentration in said retroviral-vector-free culture medium in the range of from 5 to 20 mM, lactate concentration in said medium below about 35 mM, glutamine concentration in said medium in the range of from 1 to 3 mM, and ammonia concentration in said medium below 2.5 mM.

20. The method of claim 6, said culture comprising human stromal cells in an amount of $10^{-3}$ to $10^{-1}$ (stromal cells/total cells).

* * * * *

UNITED STATES PATENT AND TRADEMARK OFFICE
CERTIFICATE OF CORRECTION

PATENT NO. : 5,399,493
DATED : March 21, 1995
INVENTOR(S) : Stephen G. Emerson, et al.

It is certified that error appears in the above-indentified patent and that said Letters Patent is hereby corrected as shown below:

On the title page, Item [54], and Column 1, Lines 2-7, the title should read:

--METHODS FOR HUMAN GENE THERAPY, INCLUDING METHODS AND COMPOSITIONS FOR THE EX VIVO REPLICATION AND STABLE GENETIC TRANSFORMATION OF HUMAN STEM CELLS, FOR THE OPTIMIZATION OF HUMAN HEMATOPOIETIC PROGENITOR CELL CULTURES AND STABLE GENETIC TRANSFORMATION THEREOF--

Signed and Sealed this

Twelfth Day of September, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,399,493
DATED : March 21, 1995
INVENTOR(S) : Stephen G. Emerson, et al.

It is certified that error appears in the above-indentified patent and that said Letters Patent is hereby corrected as shown below:

On the title page, Item [54], and Column 1, Lines 2-7, the title should read:

--METHODS FOR HUMAN GENE THERAPY, INCLUDING METHODS AND COMPOSITIONS FOR THE EX VIVO REPLICATION AND STABLE GENETIC TRANSFORMATION OF HUMAN STEM CELLS, FOR THE OPTIMIZATION OF HUMAN HEMATOPOIETIC PROGENITOR CELL CULTURES AND STABLE GENETIC TRANSFORMATION THEREOF--

On the title page, Item [75], the first inventor's city of residence should read:

--Philadelphia, PA--

This certificate supersedes Certificate of Correction issued September 12, 1995.

Signed and Sealed this

Twelfth Day of December, 1995

Attest:

BRUCE LEHMAN

Attesting Officer

Commissioner of Patents and Trademarks